United States Patent [19]

Nelson et al.

[11] Patent Number: 5,265,588
[45] Date of Patent: Nov. 30, 1993

[54] VCO DRIVEN FLYBACK CONVERTER FOR IMPLANTABLE CARDOVERTER/DEFIBRILLATOR

[75] Inventors: Gary E. Nelson, Schaumburg, Ill.; Eric Persson, Minnetonka; Joseph A. Ballis, Shoreview, both of Minn.

[73] Assignee: Medtronic, Inc., Minneapolis, Minn.

[21] Appl. No.: 823,107

[22] Filed: Jan. 15, 1992

[51] Int. Cl.⁵ ............................................. A61N 1/39
[52] U.S. Cl. ...................................................... 607/5
[58] Field of Search ....................... 128/419 D, 419 PG

[56] References Cited

U.S. PATENT DOCUMENTS

| | | | |
|---|---|---|---|
| 4,548,209 | 10/1985 | Weilders | 128/419 D |
| 4,800,883 | 1/1989 | Winstrom | 128/419 D |
| 4,830,006 | 5/1989 | Haluska | 128/419 PG |

Primary Examiner—William E. Kamm
Assistant Examiner—Scott M. Getzow
Attorney, Agent, or Firm—Reed A. Duthler; Harold R. Patton

[57] ABSTRACT

A battery powered cardioverter or defibrillator employing output capacitors for delivery of cardioversion or defibrillation pulses. The capacitors are charged by means of a step-up transformer, coupled and uncoupled from the battery by means of a voltage controlled oscillator which varies its off and on times as a function of the voltage on the battery and the voltage stored on the output capacitor to allow for rapid charging of the capacitor even under conditions of battery depletion. The voltage controlled oscillator is constructed to provide a highly accurate timing signal with a low current drain.

14 Claims, 14 Drawing Sheets

FIG. 4b

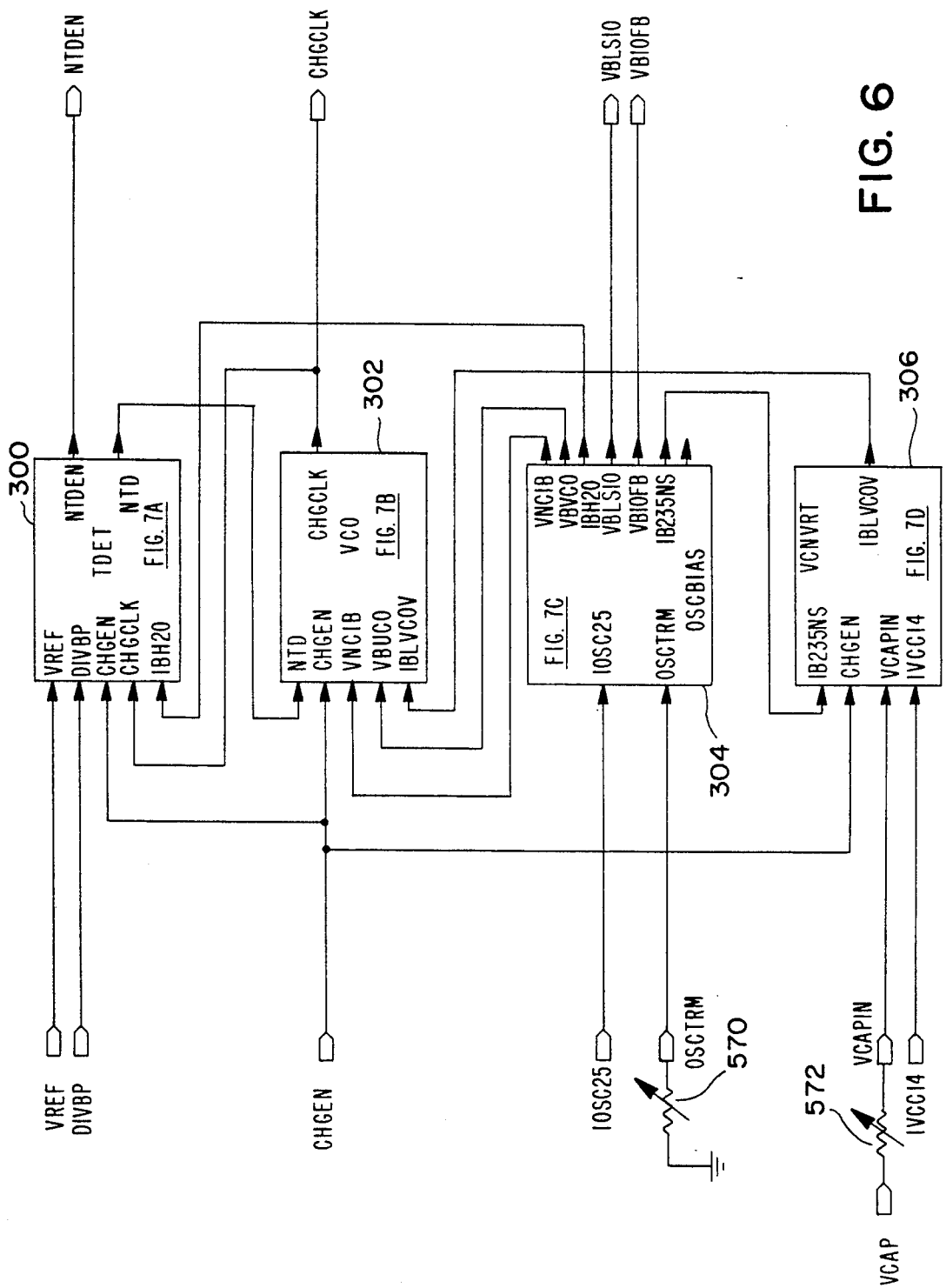

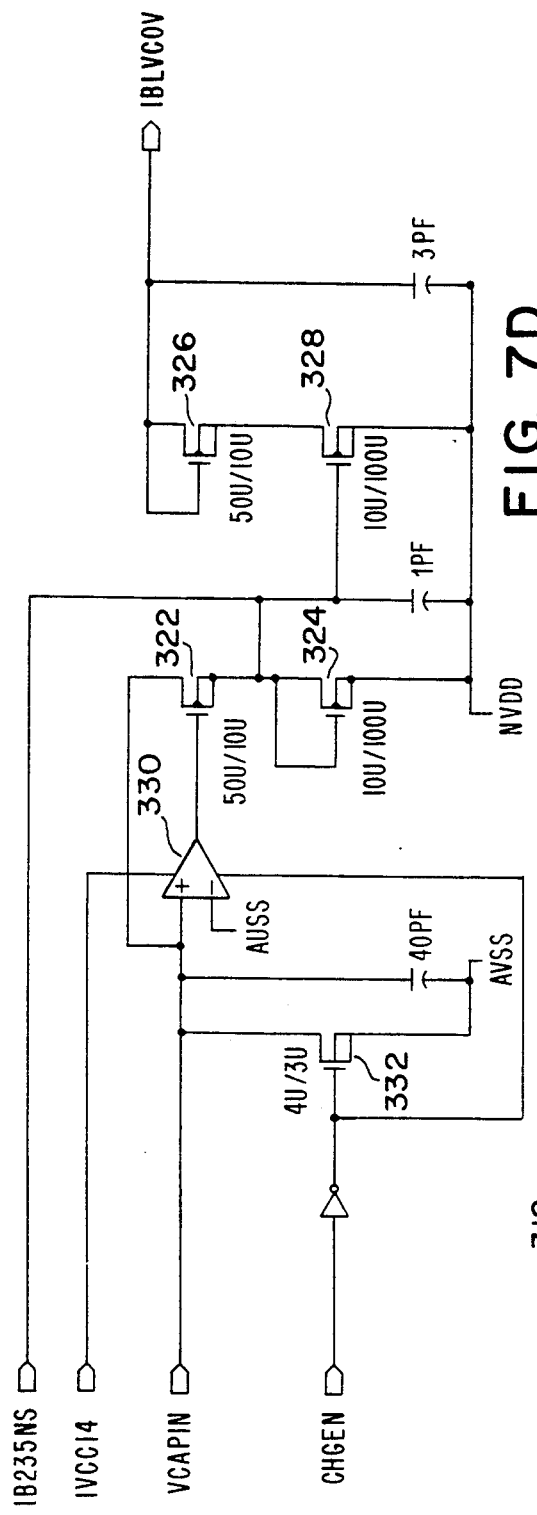
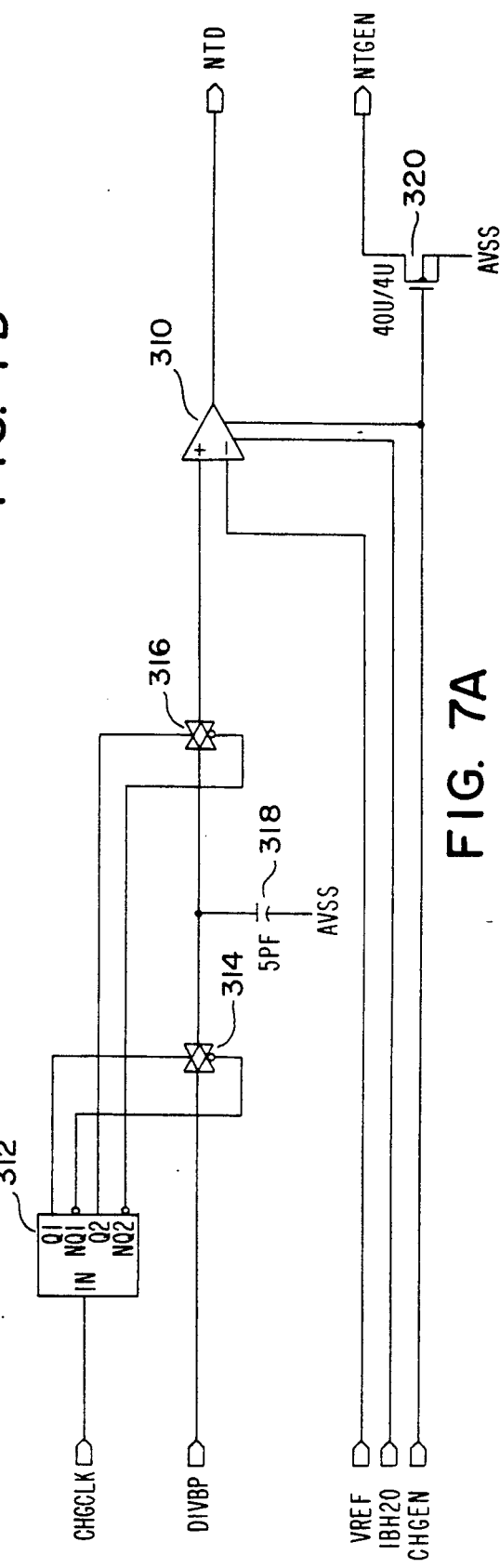
FIG. 7D
FIG. 7A

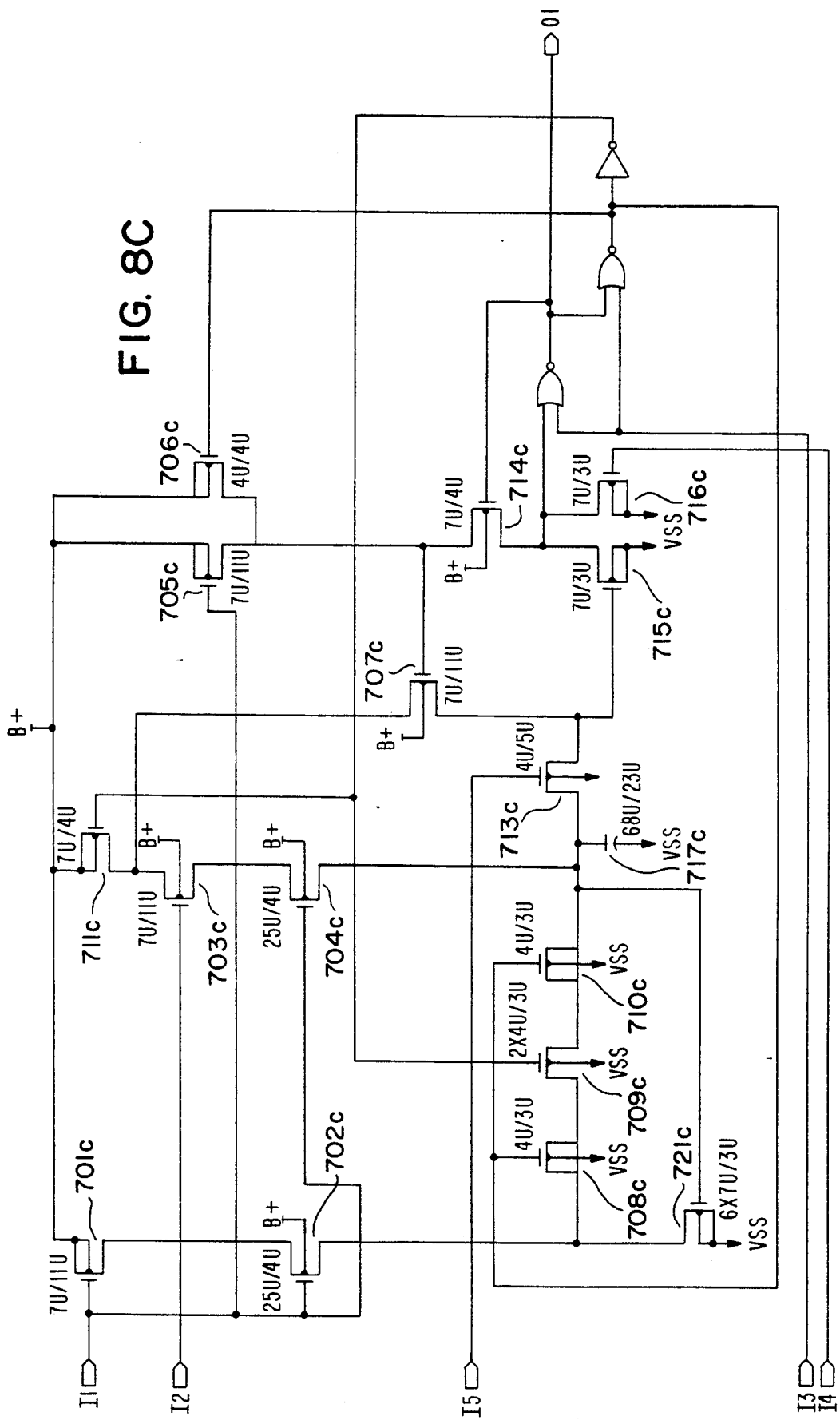

VCO DRIVEN FLYBACK CONVERTER FOR IMPLANTABLE CARDOVERTER/DEFIBRILLATOR

BACKGROUND OF THE INVENTION

1. Field of the Invention

This invention relates to an implantable medical device that delivers sufficient electrical energy to cardiac tissue to defibrillate or cardiovert tachyarrhythmias and thus restore normal sinus rhythm. An improved DC-DC converter control circuit provides a biphasic shock.

2. Description of the Prior Art

Implantable medical devices for the therapeutic stimulation of the heart are will known in the art from U.S. Pat. No. 4,253,466 issued to Hartlaub et al, which discloses a programmable demand pacemaker. The demand pacemaker delivers electrical energy (5-25 microjoules) to the heart to initiate the depolarization of cardiac tissue. This stimulating regime is used to treat heart block by providing electrical stimulation in the absence of naturally occurring spontaneous cardiac depolarizations.

Another form of implantable medical device for the therapeutic stimulation of the heart is the automatic implantable defibrillator (AID) described in U.S. Pat. No. 27,757 to Mirowski, et al and the later U.S. Pat. No. 4,030,509 to Heilman et al. These AID devices deliver energy (40 joules) to the heart to interrupt ventricular fibrillation of the heart. In operation, the AID device detects the ventricular fibrillation and delivers a non-synchronous high-voltage pulse to the heart through widely spaced electrodes located outside of the heart, thus mimicking transthoracic defibrillation. The Heilman et al technique requires both a limited thoracotomy to implant an electrode near the apex of the heart and a pervenous electrode system located in the superior vena cava of the heart.

Another example of a prior art implantable cardioverter includes the pacemaker/cardioverter/defibrillator taught by U.S. Pat. No. 4,375,817 to Engle et al. This device detects the onset of tachyarrhythmia and includes means to monitor or detect the progression of the tachyarrhythmia so that progressively greater energy levels may be applied to the heart to interrupt a ventricular tachycardia or fibrillation.

A further example is that of an external synchronized cardioverter, described in "Clinical Application of Cardioversion" in *Cardiovascular Clinics*, 1970, Vol. 2, pp. 239-260 by Douglas P. Zipes. This external device provides cardioversion shocks synchronized with ventricular depolarization to ensure that the cardioverting energy is not delivered during the vulnerable T-wave portion of the cardiac cycle.

Still another example of a prior art implantable cardioverter includes the device disclosed in U.S. Pat. No. 4,384,585 to Douglas P. Zipes. This device includes circuitry to detect the intrinsic depolarizations of cardiac tissue and includes pulse generator circuitry to deliver moderate energy level stimuli (in the range of (0.1-10 joule) to the heart synchronously with the detected cardiac activity.

The functional objective of this stimulating regimen is to depolarize areas of the myocardium involved in the genesis and maintenance of re-entrant or automatic tachyarrhythmias at lower energy levels and with greater safety than is possible with nonsynchronous cardioversion. Nonsynchronous cardioversion always incurs the risk of precipitating ventricular fibrillation and sudden death. Synchronous cardioversion delivers the shock at a time when the bulk of cardiac tissue is already depolarized and is in a refractory state. Other examples of automatic implantable synchronous cardioverters include Charms U.S. Pat. No. 3,738,370.

It is expected that the safety inherent in the use of lower energy levels, the reduced trauma to the myocardium, and the smaller size of the implanted device will expand the indications for use for this device beyond the patient base of prior art automatic implantable defibrillators. Since many episodes of ventricular fibrillation are preceded by ventricular (and in some cases, supraventricular) tachycardias, prompt termination of the tachycardia may prevent ventricular fibrillation.

Consequently, current devices for the treatment of tachyarrhythmias include the possibility of programming staged therapies of antitachycardia pacing regimens, along with cardioversion energy and defibrillation energy shock regimens in order to terminate the arrhythmia with the most energy efficient and least traumatic therapies (if possible). In addition, current devices envisage inclusion of single or dual chamber bradycardia pacing therapies, all of which are described, for example, in U.S. Pat. No. 4,800,833 to Winstrom, U.S. Pat. No. 4,830,006 to Haluska et al, and U.S. patent application Ser. No. 07/612,758 filed Nov. 14, 1990, and incorporated herein by reference.

Furthermore, as described in the '833 and '006 patents and the '758 application, considerable study has been undertaken to devise the most efficient electrode systems and shock therapies.

Initially, implantable cardioverters and defibrillators were envisioned as operating with a single pair of electrodes applied on or in the heart. Examples of such systems are disclosed in the aforementioned '757 and '509 patents wherein shocks are delivered between an electrode placed in or on the right ventricle and a second electrode placed outside the right ventricle. Studies have indicated that two electrode defibrillation systems often require undesirably high energy levels to effect defibrillation. In an effort to reduce the amount of energy required to effect defibrillation, numerous suggestions have been made with regard to multiple electrode systems. For example, sequential pulse multiple electrode systems are disclosed in U.S. Pat. No. 4,291,699, issued to Geddes, et al, in U.S. Pat. No. 4,708,145, issued to Tacker, et al, in U.S. Pat. No. 4,727,877 issued to Kallock and in U.S. Pat. No. 4,932,407 issued to Williams. Sequential pulse systems operate based on the assumption that sequential defibrillation pulses, delivered between differing electrode pairs have an additive effect such that the overall energy requirements to achieve defibrillation are less than the energy levels required to accomplish defibrillation using a single pair of electrodes.

An alternative approach to multiple electrode, sequential pulse defibrillation is disclosed in U.S. Pat. No. 4,641,656 issued to Smits and also in the above-cited '407 patent. This defibrillation method may conveniently be referred to as multiple electrode, simultaneous pulse defibrillation, and involves the delivery of defibrillation pulses simultaneously between two different pairs of electrodes. For example, one electrode pair may include a right ventricular electrode and a coronary sinus electrode, and the second electrode pair may include a right ventricular electrode and a subcutaneous patch electrode, with the right ventricular electrode serving as a common electrode to both electrode pairs. An alternative multiple electrode, single path, biphasic pulse system is disclosed in U.S. Pat. No. 4,953,551 issued to Mehra, et al, employing right ventricular, superior vena cava and subcutaneous patch electrodes.

In the above-cited prior simultaneous pulse, multiple electrode systems, delivery of the simultaneous defibrillation pulses is accomplished by simply coupling two of the electrodes together. For example, in the above-cited '551 patent, the superior vena cava and subcutaneous patch electrodes are electrically coupled, and a pulse is delivered between these two electrodes and the right ventricular electrode. Similarly, in the above-cited '407 patent, the subcutaneous patch and coronary sinus electrodes are electrically coupled together, and a pulse is delivered between these two electrodes and a right ventricular electrode.

The above incorporated '758 application discloses a pulse generator for use in conjunction with an implantable cardioverter/defibrillator which is capable of providing all three of the defibrillation pulse methods described above, with a minimum of control and switching circuitry. The output stage is provided with two separate output capacitors, which are sequentially discharged during sequential pulse defibrillation and simultaneously discharged during single or simultaneous pulse defibrillation. The complexity of these stimulation therapy regimens require rapid and efficient charging of high voltage output capacitors from low voltage battery power sources.

Typically, the electrical energy to power an implantable cardiac pacemaker is supplied by low voltage, low current, long-lived power source, such as a lithium iodine pacemaker battery of the types manufactured by Wilson Greatbatch Ltd. and Medtronic, Inc. While the energy density of these power sources is relatively high, they are not designed to be rapidly discharged at high current drains, as would be necessary to directly cardiovert the heart with cardioversion energies in the range of 0.1–10 joules. Higher energy density battery systems are known which can be more rapidly discharged, such as lithium thionyl chloride power sources. However, none of the available implantable, hermetically sealed power sources have the capacity to directly provide the cardioversion energy necessary to deliver an impulse of the aforesaid magnitude to the heart following the onset of tachyarrhythmia.

Generally speaking, it is necessary to employ a DC-DC converter to convert electrical energy from a low voltage, low current power supply to a high voltage energy level stored in a high energy storage capacitor. A typical form of DC-DC converter is commonly referred to as a "flyback" converter which employs a transformer having a primary winding in series with the primary power supply and a secondary winding in series with the high energy capacitor. An interrupting circuit or switch is placed in series with the primary coil and battery. Charging of the high energy capacitor is accomplished by inducing a voltage in the primary winding of the transformer creating a magnetic field in the secondary winding. When the current in the primary winding is interrupted, the collapsing field develops a current in the secondary winding which is applied to the high energy capacitor to charge it. The repeated interruption of the supply current charges the high energy capacitor to a desired level over time.

In U.S. Pat. No. 4,548,209 to Wielders et al, as well as in the above-referenced '883 patent, charging circuits are disclosed which employ flyback oscillator voltage converters which step up the power source voltage and apply charging current to output capacitors until the voltage on the capacitors reaches the programmed shock energy level.

Specifically, in the charging circuit 34 of FIG. 4 of the '209 patent, the two series connected lithium thionyl chloride batteries 50 and 52 are shown connected to the primary coil 54 of transformer 56 and to the power FET transistor switch 60. The secondary coil 58 is connected through diode 62 to the cardioversion energy storage capacitor 64. Very generally, the flyback converter works as follows: When switch 60 is closed, current $I_p$ passing through the primary winding 54 increases linearly as a function of the formula $V=L_p dI/dt$. When FET 60 is opened, the flux in the core of the transformer 56 cannot change instantaneously so a complimentary current $I_s$ which is proportional to the number of windings of the primary and secondary coils 54 and 58 respectively starts to flow in the secondary winding 58 according to the formula $(N_p/N_S)I_p$. Simultaneously, voltage in the secondary winding is developed according to the function $V_s=L_s dU/dt_s$. The cardioversion energy storage capacitor 64 is charged thereby to the programmed voltage.

The power FET is switched "on" at a constant frequency of 32 KHz for a duration or duty cycle that varies as a function of the voltage of the output capacitor reflected back into the primary coil 54 circuit. The on-time of power FET 60 is governed by the time interval between the setting and resetting of flip-flop 70 which in turn is governed either by the current $I_p$ flowing through the primary winding 54 or as a function of a time limit circuit, which contains further circuitry to vary the time limit with battery impedance (represented schematically by resistor 53). In both cases, the on-time varies from a maximum to a minimum interval as the output circuit increases to its maximum voltage.

The '883 and '006 patents disclose a variable duty cycle flyback oscillator voltage converter, where the current in the primary coil circuit (in the case of the '883 patent) or the voltage on a secondary coil (in the case of the '006 patent) is monitored to control the duty cycle of the oscillator. In the '883 circuit the "on" time of the oscillator is constant and the "off" time varies as a function of the monitored current through the transformer.

In the '006 patent, a secondary coil is added to power a high voltage regulator circuit that provides V+ to a timer circuit and components of the high voltage oscillator. This high voltage power source allows the oscillator circuit to operate independently of the battery source voltage which may deplete over time. The inclusion of a further secondary winding on an already relatively bulky transformer is disadvantageous from size and efficiency standpoints.

SUMMARY OF THE INVENTION

Accordingly, it is an object of the present invention to provide a highly energy efficient and compact pulse generator suitable for use in an implantable automatic cardioverter/defibrillator.

It is another object to provide a cardioversion/defibrillation pulse generator that includes improved voltage conversion, operational stability and accuracy independent of the magnitude of the pulses to be applied to the heart.

It is a further object to provide a pulse generator that provides rapid and efficient DC-DC conversion without the addition of bulky components.

The above objects and attendant advantages are achieved by providing an apparatus which generates single phase or multiphasic simultaneous or sequential, defibrillation pulse waveforms having selected programmable parameters of magnitude, polarity, and duration. The apparatus includes a charging circuit connected to a charge-storing circuit which provides multiple different output potentials. The charging circuit charges the charge storing circuit to a selected charge level in response to a control signal generated upon the detection of tachycardia or fibrillation. When the charge storing circuit is charged to selected charge level, a pulse generator selectively and sequentially connects and disconnects the charge storing circuit through conduction device to the stimulation electrodes, to deliver the programmed cardioversion or defibrillation waveform to the heart.

More particularly in the context of such apparatus the present invention comprises a flyback transformer voltage multiplier in which a transformer primary winding is alternately tied to ground and the positive battery terminal to build a magnetic field and then open circuited to allow the field to collapse to create a high voltage in the secondary winding to charge one or more output capacitors comprising the charge-storing circuit. The frequency at which the primary is driven ("on" time) and then open circuited ("off" time) is controlled by a VCO whose period equals a constant "on" time plus a variable "off" time which is inversely proportional to the DC value Vm of the voltage stored on the output capacitors. The expression for the period of the VCO is:

$$\text{Period} = \text{Ton} + \frac{K}{IF + Vm/R}, \text{ where:}$$

Ton = the fixed "on" time;

IF = a constant current used to set the maximum "off" time when Vm=0;

K = a constant used with IF to set the maximum "off" time when Vm=0; and

R = value of the resistor placed between Vm and ground to set a current which adds to IF to decrease the "off" time.

The novel elements believed to be characteristic of the present invention are set forth in the appended claims. The invention itself, together with additional objects and attendant advantages, will best be understood by reference to the following detailed description, which, when taken in conjunction with the accompanying drawings, describes a presently preferred embodiment.

BRIEF DESCRIPTION OF THE DRAWINGS

Reference is now made to the accompanying detailed drawings of the preferred embodiments in which like reference numerals represent like or similar parts throughout, and wherein:

FIGS. 4A and 4B are an electrical schematic diagram of the high voltage charging circuit, output capacitor bank and high voltage output circuit of the present invention;

FIG. 6 is a schematic block diagram of timing and control circuitry employed in conjunction with FIGS. 5 and 4 in charging up the output capacitor bank;

FIGS. 7A to 7D are electrical schematic diagrams of the components included in the blocks of FIG. 6;

FIGS. 8A–8C are electrical schematic diagrams of components depicted in FIG. 7B.

DETAILED DESCRIPTION OF THE PREFERRED EMBODIMENT

Figure 1:
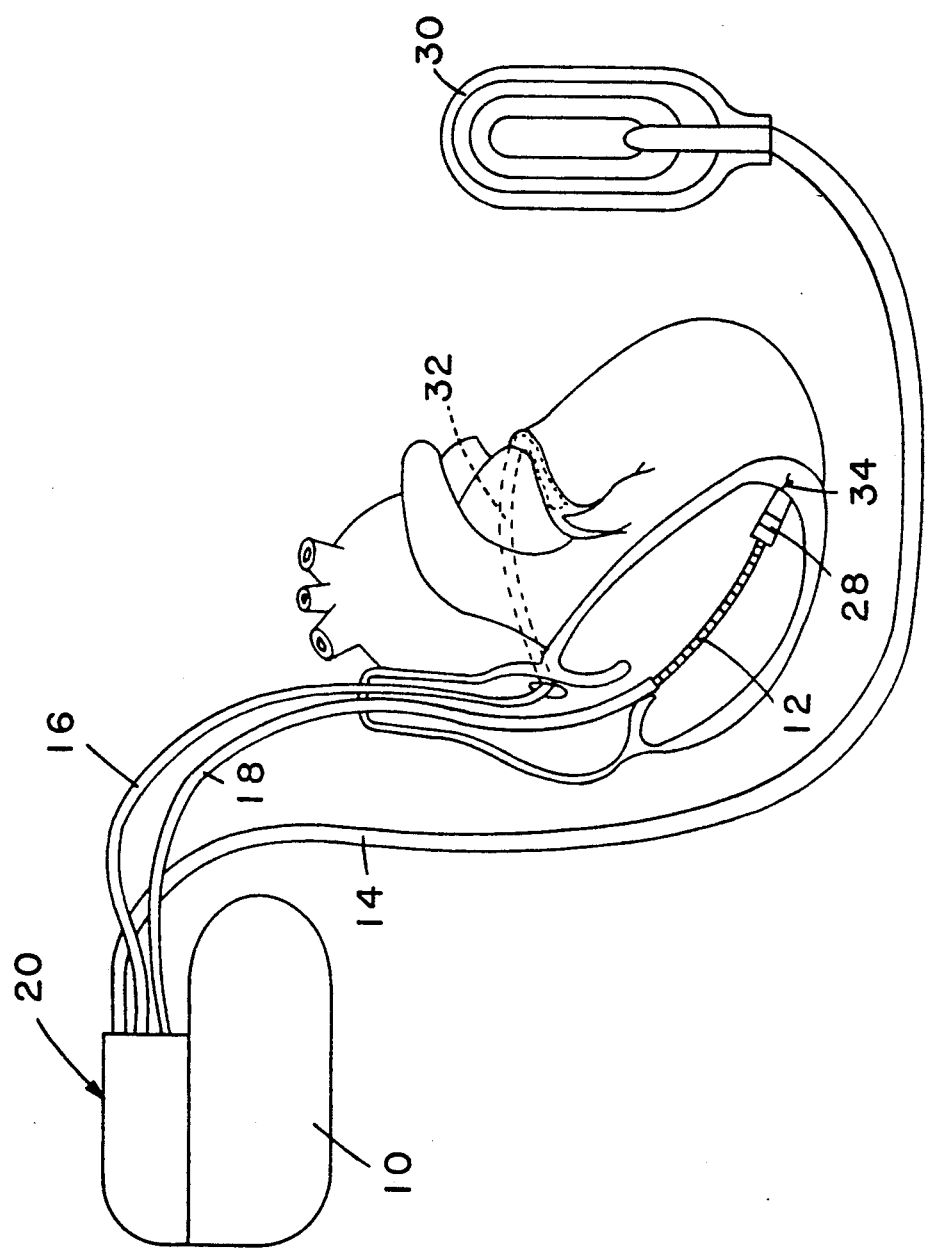
FIG. 1 is a drawing illustrating the physical components of a pacemaker/cardioverter/defibrillator and lead system of the type in which the present invention may be advantageously practiced.

FIG. 1 illustrates an implantable pacemaker/cardioverter/defibrillator 10, its associated electrical leads 14, 16 and 18, and their relationship to a human heart 12 and corresponds to FIG. 1 of the '758 application. The leads are coupled to the pacemaker/cardioverter/defibrillator 10 by means of a multi-lumen connector block 20, which contains separate connector ports for each of the three leads illustrated. Lead 14 is coupled to a subcutaneous electrode 30, which is intended to be mounted subcutaneously in the region of the left chest. Lead 16 is a coronary sinus lead employing an elongated coil electrode which is located in the coronary sinus and great vein region of the heart. The location of the electrode is illustrated in broken line format at 32, and extends around the heart from a point within the opening of the coronary sinus to a point in the vicinity of the left atrial appendage.

Lead 18 is provided with an elongated electrode coil 28 which is located in the right ventricle of the heart. Lead 18 also includes a stimulation electrode 34 which takes the form of an advanceable helical coil which is screwed into the myocardial tissue of the right ventricle. Lead 18 may also include one or more additional electrodes for near and far field electrogram sensing. A more detailed description of the leads illustrated can be found in the aforementioned '407 patent. However, the invention is also believed workable in the context of multiple electrode systems employing different sets of electrodes, including superior vena cava electrodes and epicardial patch electrodes.

In the system illustrated, cardiac pacing pulses are delivered between helical electrode 34 and elongated electrode 28. Electrodes 28 and 34 are also employed to sense electrical signals indicative of ventricular contractions. As illustrated, it is anticipated that the right ventricular electrode 28 will serve as the common electrode during sequential and simultaneous pulse multiple electrode defibrillation regimens. For example, during a simultaneous pulse defibrillation regimen, pulses would simultaneously be delivered between electrode 28 and electrode 30 and between electrode 28 and electrode 32.

during sequential pulse defibrillation, it is envisioned that pulses would be delivered sequentially between subcutaneous electrode 30 and electrode 28 and between coronary sinus electrode 32 and right ventricular electrode 28. Single pulse, two electrode defibrillation pulse regimens may be also provided, typically between electrode 28 and coronary sinus electrode 32. Alternatively, single pulses may be delivered between electrodes 28 and 30. The particular interconnection of the electrodes to the implantable pacemaker/cardioverter/defibrillator will depend somewhat on which specific single electrode pair defibrillation pulse regimen is believed more likely to be employed.

Figure 2:
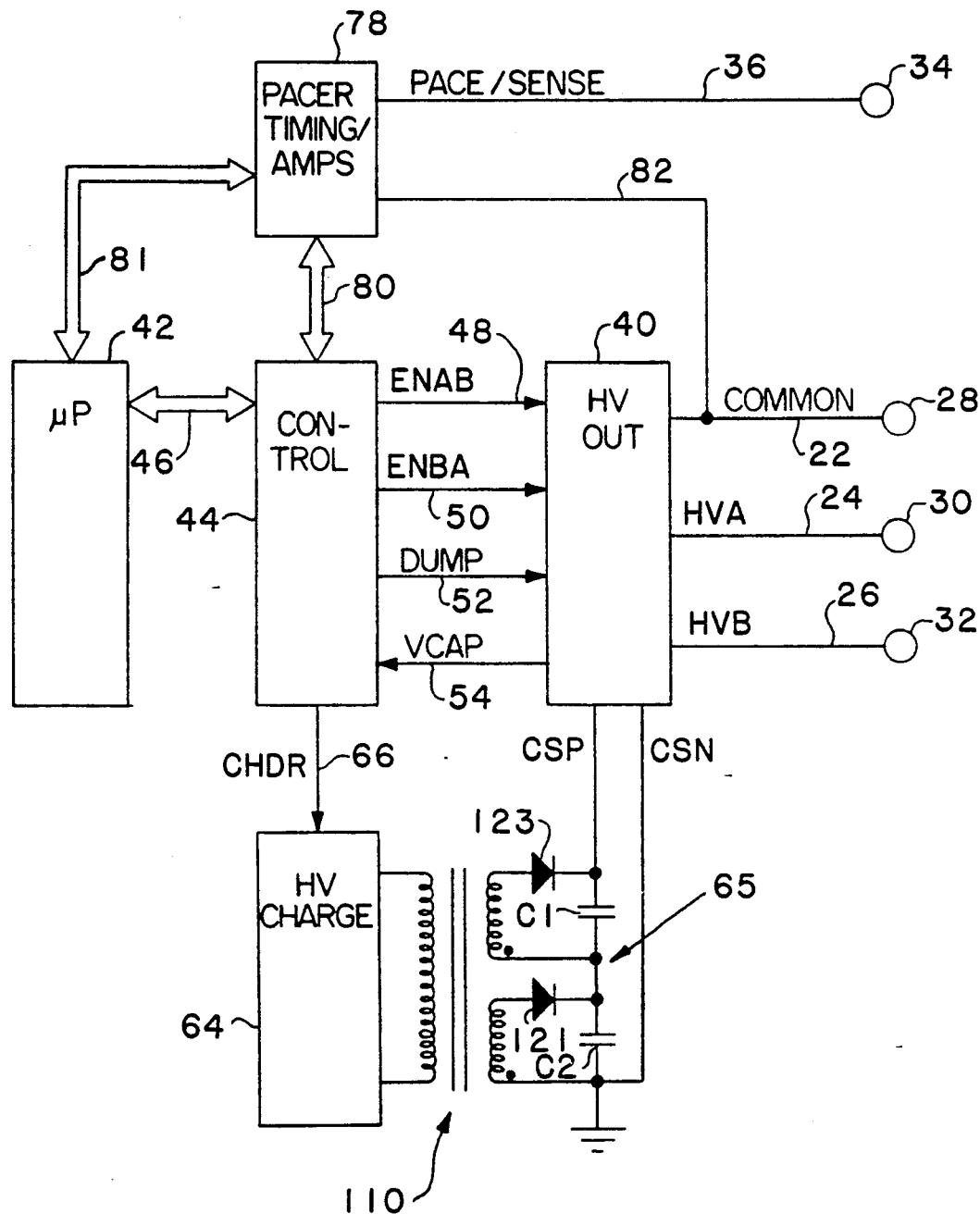
FIG. 2 is a functional block diagram illustrating the interconnection of the improved voltage conversion circuitry of the present invention with the primary functional components of an implantable pacemaker/cardioverter/defibrillator.

FIG. 2 is a block diagram illustrating the interconnection of a high voltage output circuit 40, a high voltage charging circuit 64 and capacitor bank 65 according to one embodiment of the present invention with a prior art implantable pacemaker/cardioverter/defibrillator. As illustrated, the device is controlled by means of a stored program in a microprocessor 42, which performs all necessary computational functions within the device. Microprocessor 42 is linked to control circuitry 44 by means of a bi-directional data/control bus 46, and thereby controls operation of the output circuitry 40 and the high voltage charging circuitry 64. On reprogramming of the device or on the occurrence of signals indicative of delivery of cardiac pacing pulses or of the occurrence of cardiac contractions, pace/sense circuitry 78 will awaken microprocessor 42 to perform any necessary mathematical calculations, to perform tachycardia and fibrillation detection procedures and to update the time intervals controlled by the timers in pace/sense circuitry 78. The basic operation of such a system in the context of an implantable pacemaker/cardioverter/defibrillator may correspond to any of the systems known to the art, and in more particular may correspond generally to those illustrated in the aforementioned '209, '585, '006, '883 and '817 patents and U.S. Pat. No. 4,693,253, issued to Adams, all of which are incorporated herein by reference in their entireties.

The control circuitry 44 provides three signals of primary importance to the output circuitry 40 of the present invention. These include the first and second control signals discussed above, labeled here as ENAB, line 48, and ENBA, line 50. Also of importance is DUMP line 52 which initiates discharge of the output capacitors and VCAP line 54 which provides a signal indicative of the voltage stored on the output capacitors C1, C2, to the control circuitry 44. The defibrillation electrodes 28, 30 and 32 illustrated in FIG. 1, above, are shown coupled to the output circuitry 40 by means of conductors 22, 24 and 26. For ease of understanding, these conductors are also labeled as "COMMON", "HVA" and "HVB". However, other configurations are also possible. For example, subcutaneous electrode 30 may be coupled to HVB conductor 26, to allow for a single pulse regimen to be delivered between electrodes 218 and 30. During a logic signal on ENAB, line 48, a cardioversion/defibrillation pulse is delivered between electrode 30 and electrode 28. During a logic signal on ENBA, line 50, a cardioversion/defibrillation pulse is delivered between electrode 32 and electrode 28.

The output circuitry of the present invention includes a capacitor bank, including capacitors C1 and C2 and diodes 121 and 123, used for delivering defibrillation pulses to the electrodes. Alternatively, the capacitor bank may include a further set of capacitors as depicted in the above referenced '758 application. In FIG. 2, the capacitor bank is illustrated in conjunction with the high voltage charging circuitry 64, controlled by the control/timing circuitry 44 by means of CHDR line 66. As illustrated, capacitors C1 and C2 are charged by means of a high frequency, high voltage transformer 110. Proper charging polarities are maintained by means of the diodes 121 and 123. VCAP line 54 provides a signal indicative of the voltage on the capacitor bank, and allows for control of the high voltage charging circuitry and for termination of the charging function when the stored voltage equals the programmed charging level.

Pace/sense circuitry 78 includes an R-wave amplifier according to the prior art, or more advantageously as disclosed in co-pending, commonly assigned application Ser. No. 07/612,670 by Keimel et al, for an "Apparatus for Monitoring Electrical Physiological Signals," filed Nov. 14, 1990, which is incorporated herein by reference in its entirety. However, the present invention is believed workable in the context of any known R-wave amplification system. Pace/sense circuitry 78 also includes a pulse generator for generating cardiac pacing pulses, which may also correspond to any known cardiac pacemaker output circuitry and includes timing circuitry for defining ventricular pacing intervals, refractory intervals and blanking intervals, under control of microprocessor 42 via control/data bus 80. Control signals triggering generation of cardiac pacing pulses by pace/sense circuitry 78 and signals indicative of the occurrence of R-waves, from pace/sense circuitry 78 are communicated to control circuitry 44 by means of a bi-directional data bus 81. Pace/sense circuitry 78 is coupled to helical electrode 34 illustrated in FIG. 1 by means of a conductor 36. Pace/sense circuitry 78 is also coupled to ventricular electrode 28, illustrated in FIG. 1, by means of a conductor 82, allowing for bipolar sensing of R-waves between electrodes 34 and 28 and for delivery of bipolar pacing pulses between electrodes 34 and 28, as discussed above.

Figure 3:
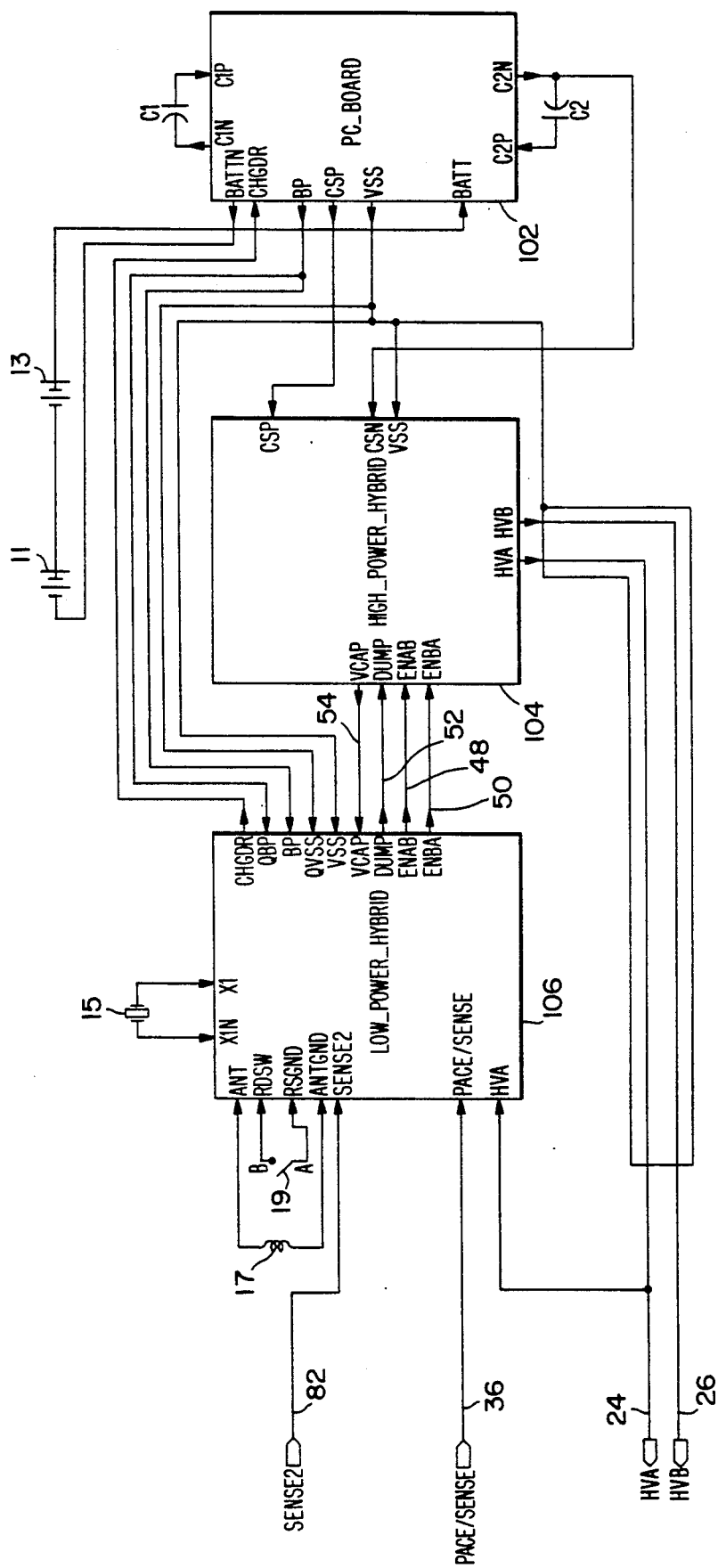
FIG. 3 is a schematic block diagram of the components of a preferred embodiment of the pacemaker/cardioverter/defibrillator employing a high voltage charging circuit of the present invention.

Turning now to FIGS. 3 through 8, the best mode of practicing the present invention known to the inventors is illustrated in conjunction with the design of a pacemaker/cardioverter/defibrillator employing the major components depicted in FIG. 3. Inasmuch as the present invention constitutes improvement in the voltage conversion circuitry and may be practiced in connection with any cardioverter or defibrillator design, the particular circuitry involved in the implementation of the voltage conversion circuitry and circuitry which supplies signals to operate the voltage conversion circuitry are shown in specific detail. In the description of the preferred embodiment of FIGS. 3 through 8, a number of expressions for input and output signals are used throughout, including:

CHGDR—the charge drive signal for driving the on/off switch in the primary winding of the flyback transformer at a duty cycle established by the relative on and off times.

CHGCLK—the charge clock signal from which the charge drive signal is developed.

CHGEN—the charge enable command signal for commencing the operation of the high voltage charge voltage converter.

VCAP—the signal developed from the voltage on the high voltage output capacitors C1 and C2.

VSS—VSS is the circuit ground which may also appear and named QVSS and may be connected to BATTN.

BATT—battery positive power supply which may also appear as B+ or as BP.

BATTN—battery negative power supply.

TDET—battery voltage threshold detection circuit providing NTD signal for controlling CHDR "on" time established by VCO.

ENBA—An enable signal commanding capacitor discharge from HVB to HVA.

ENAB—An enable signal commanding capacitor discharge from HVA to HVB.

CSP—charge store positive terminal.

CSN—charge store negative terminal.

Figure 5:
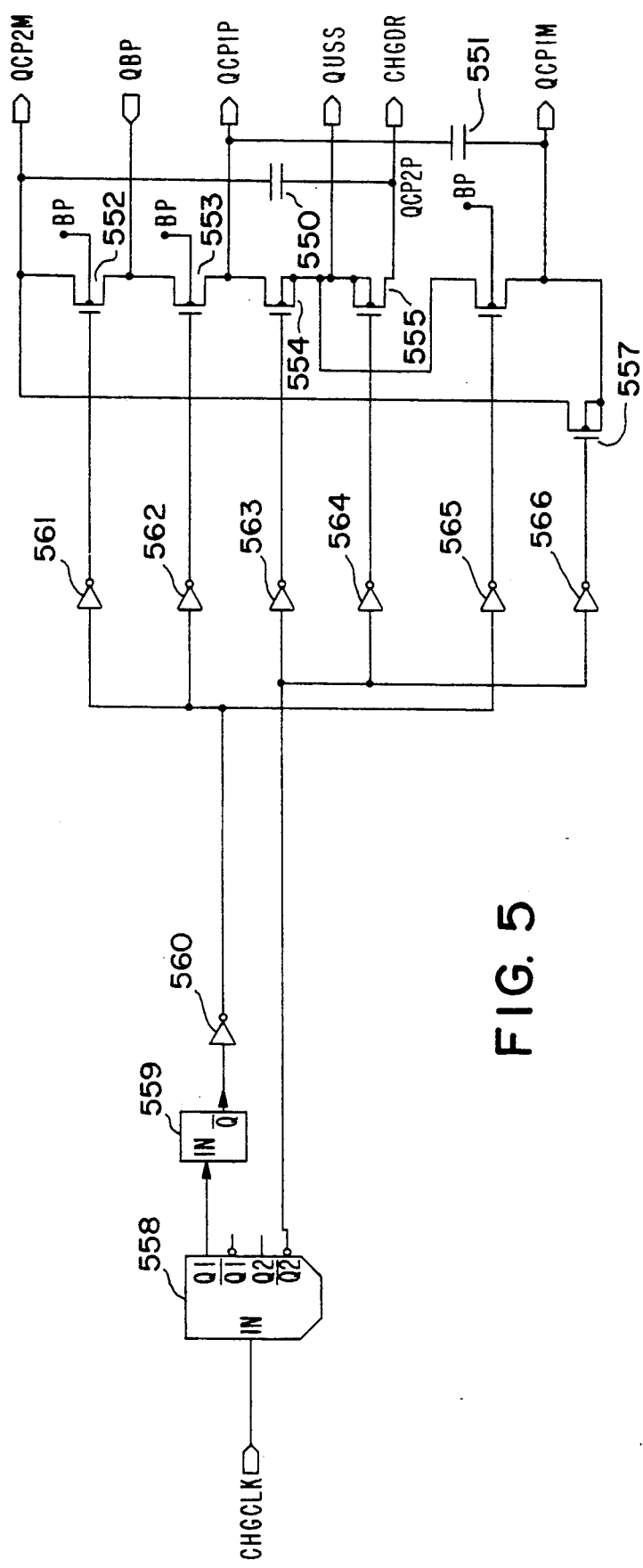
FIG. 5 is an electrical schematic diagram of a circuit for generating the charge drive signal for charging up the output capacitor bank of FIG. 4A and FIG. 4B in accordance with the present invention.

QBP—battery supply to the charge driver functional block diagram of FIG. 5 connected separately by a high current conductor path to the battery power source.

VDD—internally generated programmable regulated power supply.

OSCTRIM—an external oscillator trim resister for trimming the delay stages in the regulator oscillator and voltage controlled oscillator of FIG. 6 to specification.

VICNVRT—voltage conversion block for converting high voltage VCAP to a bias current for controlling the "off" time (ref. page 11) as generated by the VCO.

VCO—voltage controlled oscillator

VBVCO—a bias voltage for VCO delay circuits.

VNC1B—a bias voltage for DEL1-DEL3, and DELVAR circuits.

DELVAR5—delay circuits in the VCO which are used to control the "on" time as defined by the VCO DELVAR3—further delay circuit in the VCO DELVAR—delay circuit in the VCO responsive to IBLVCOV, used to limit "off" time as defined by the VCO.

NPD—a binary signal which is "high" when VIVVP is greater than VREF and is "low" when VIVVP is less than the VREF.

VIVVP—a signal equal to one-half the actual BATT voltage.

VREF—a reference voltage for comparison to VIVVP.

DUMP—the DUMP signal initiates the internal self discharge of the capacitors C1, C2 to a load impedance.

Other acronyms may appear in the description of the following drawings which will be explained as necessary to understand the manner in which the present invention may be practiced in its preferred embodiment.

Turning now to FIG. 3, the major components of the pacemaker/cardioverter/defibrillator of the present invention are depicted and they include the batteries 11 and 13, the PC board 102, the high voltage output capacitors C1, C2, the high power hybrid board 104, the low power hybrid board 106, the crystal 15, the antenna 17, and the reed switch 19. The batteries 11 and 13 are coupled to the BATT and BATTN inputs of the PC board 102. The crystal 15 is coupled to the X1 and X1N inputs of the low power hybrid 106. The antenna 17 is coupled between the ANT and ANTGND inputs of low power hybrid 106 and the reed switch 19 is coupled between the RDSW and RSGND inputs of low power hybrid 106. The PACE/SENSE line 36 is coupled to the PACE/SENSE input terminals. Similarly, the HVA line 24 and HVB line 26 are coupled to the HVA and HVB output terminals of low power hybrid 106. The HVA and HVB output signals applied to electrodes 30 and 32 (FIG. 1) are generated from the high power hybrid 104.

The low power hybrid 106 includes the basic timing and control circuitry of the system, including the programming and telemetry functions, the electrogram sensing and pacing functions, the microprocessor and RAM/ROM memories, all implemented in both digital and analog circuits corresponding to blocs 42, 44 and 78 in FIG. 2. The low power hybrid 106 includes the circuits of FIGS. 5, 6 and 7, which develop the CHGDR signal as well as the VCAP, DUMP, ENBA and ENAB signals relevant to the operation of the voltage converter of the present invention.

The PC board 102 corresponds to the high voltage charging block 64 in FIG. 2, and also includes the step up transformer 110 and diodes 121, 123. The relatively large output capacitors C1, C2 are electrically connected to the PC board 102 through the input terminals CIN and CIP and C2N and C2P, respectively. The PC board 102 presents the charge storage positive and negative signals CSP and CSN, respectively, to the high power hybrid 104. PC board 102 also includes an on-off control switch, responsive to the CHGDR signal from the low power hybrid 106, for supplying stepped up, rectified current to the output capacitors C1, C2, across which the voltage signals CSP, CSN are developed.

The high power hybrid 104 corresponds to the high voltage output block 40 illustrated in FIG. 2 and includes switching circuitry for delivery of voltage stored in capacitors C1 and C2 as monophasic and biphasic output pulses. Delivery of the output pulses is controlled by the low power hybrid 106 via ENAB and ENBA lines 48 and 50, respectively.

Figure 4A:
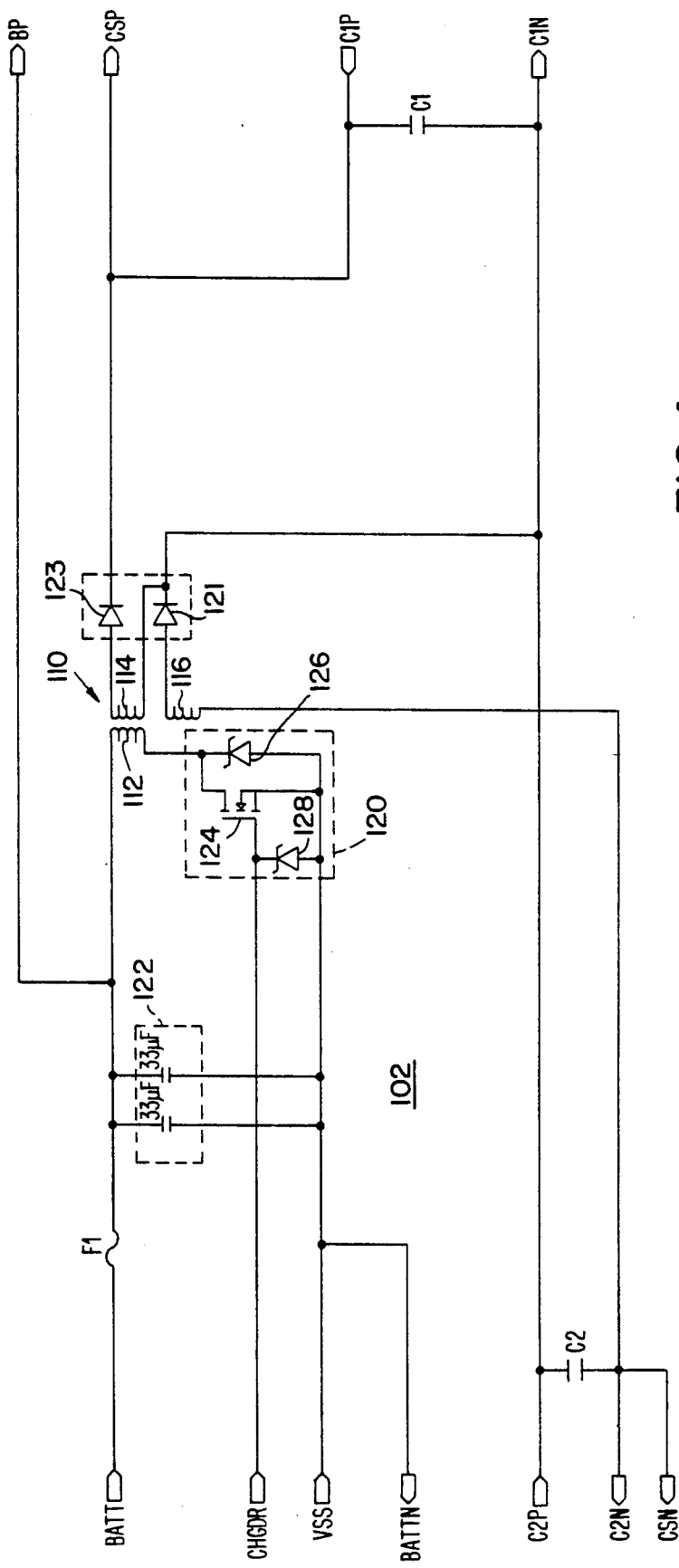

FIG. 4A illustrates the PC board 102 in more detail. The step-up transformer 110 includes a primary winding 112 and secondary windings 114, 116, which are coupled through diodes 121 and 123 to the output capacitors C1, C2. As described above, the voltage across output capacitors C1, C2 is applied at output terminals CSP, CSN to correspondingly labeled terminals in FIG. 4B.

The primary winding 112 is coupled at one terminal to the power supply BATT input terminal through a fuse link F1 and at its other terminal to the BATTN/VSS terminals through the duty cycle switching circuit block 120. A pair of 33 microfarad capacitors 122 are coupled across the BATT and BATTN/VSS terminals.

The switching circuit 120 includes a power FET transistor 124 having its source and drain terminals coupled across a zener diode 126 in such a fashion that when the power FET 124 is rendered conductive by a CHGDR signal applied at its gate input terminal, it allows current to pass through the primary coil 112 of the step-up transformer 110. Power FET 124 preferably has a very low drain-to-source impedance when conductive and a high gate impedance. A second zener diode 128 coupled to the gate terminal of the power FET 124 and having a reverse breakdown voltage of around 10 volts limits the CHGDR voltage.

In a manner as described in the incorporated '209 patent, the switching of the power FET 124 on and off effects the charging of the output capacitors C1, C2 in a well known fashion. In accordance with the present invention, the CHGDR signal amplitude is generated as a function of the BATT voltage and a frequency which is established by a VCO as a function of the VCAP voltage. As stated hereinbefore, the "on" time of the CHGDR signal is constant and is preferably 11 microseconds (except when the BATT potential is depleted as explained hereafter), whereas the off-time is variable in inverse proportion to the VCAP value. The mathematical expression for the operation of the flyback oscillator voltage converter responding to such a charge drive signal is set forth in the Summary of the Invention above.

Figure 4B:
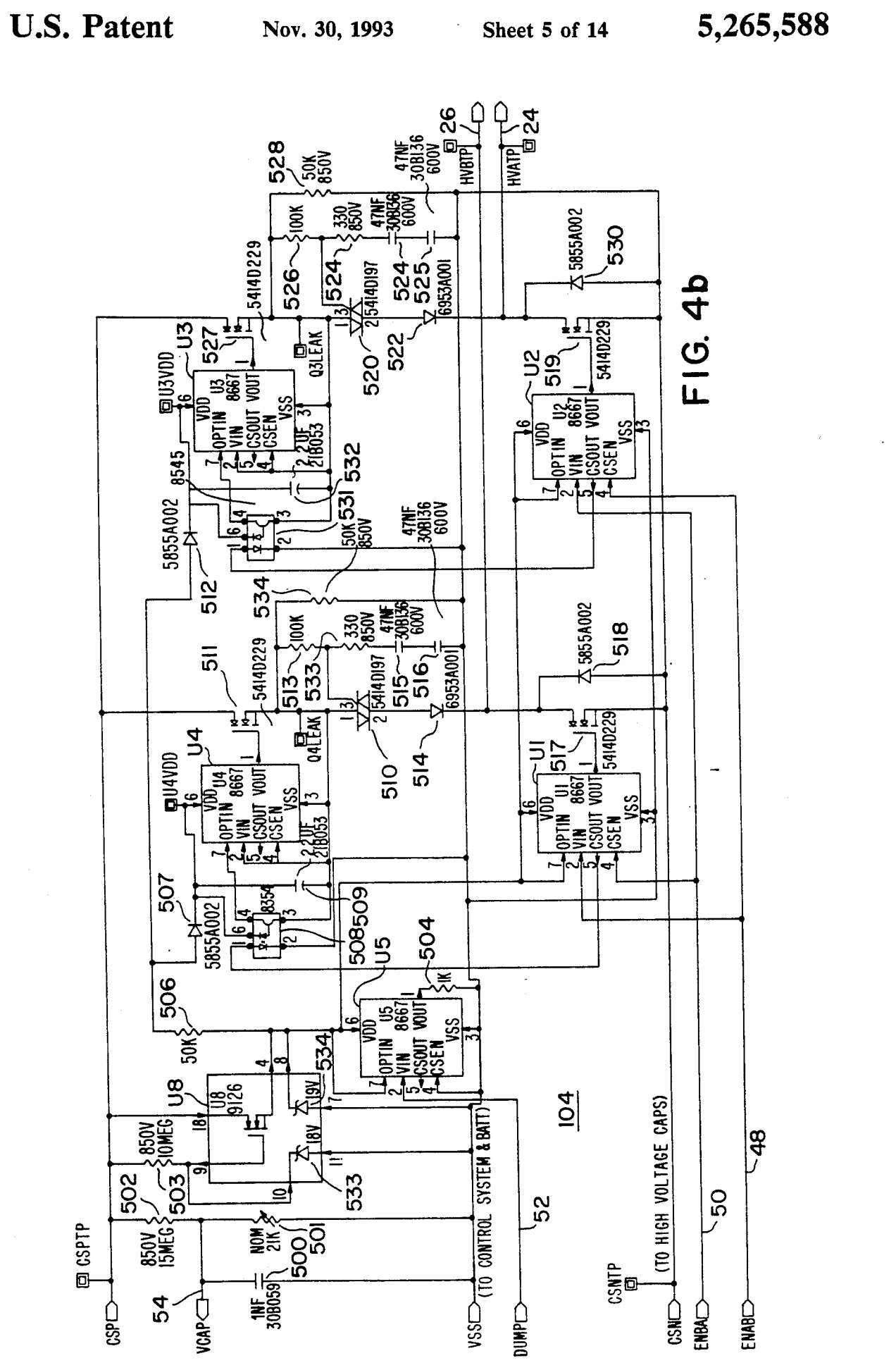

Before describing how the CHGDR signal is generated, reference is drawn to the high power hybrid schematic diagram depicted in FIG. 4B. This high power hybrid electrical schematic diagram is similar to but not identical to FIG. 3 of the above incorporated '758 application and the '551 patent. FIG. 4B is set forth in its entirety to present an alternative embodiment to the embodiment of FIG. 3 of the '758 application and the '551 patent in which the present invention may be practiced. However, it will be understood that the invention may be practiced in the context of any of the referenced voltage converters.

In particular, in FIG. 4B, the VCAP signal on line 54 is derived from and representative of the actual voltage on the output capacitors C1, C2 across terminals CSP, CSN/VSS in FIG. 4B. The VCAP signal is developed across the CSP and CSN/VSS terminals through a voltage divider comprising resistor 501 (21K ohm nominal) and resistor 502 (15 Megohm) and capacitor 500 (1 nano Farad). Thus, the VCAP signal is proportional to the "positive, summed voltages" of the capacitors C1 and C2 from FIG. 4A with respect to ground potential.

The VCAP signal is employed in the low power hybrid 106 of FIG. 3 to monitor the state of charge of the output capacitors C1 and C2 for various operations, including the determination of when the voltage on the output capacitors C1, C2 has reached the desired level to initiate the delivery of the cardioversion/defibrillation shocks through discharge of the capacitors C1, C2 for a predetermined interval. The interval may be a selected interval or may be a function of the magnitude of the VCAP signal as the capacitors are discharged. In other words, the discharge may be for a predetermined time interval or until the voltages have discharged to a desired level. By controlling the discharge level, the amount of energy delivered to the heart is directly controlled.

In FIG. 4B the voltage at terminal CSP is connected to two parallel discharge circuits and back to the terminal CSN in order to provide first and second directional discharge paths through the heart coupled between the terminals HVA and HVB. The terminals HVA and HVB are connected to the junction of the diodes 522 and 514 with the power FETs 519 and 517, respectively. The selection of the first and second discharge paths is made by the ENAB and ENBA signals. The AB discharge path is from the terminal HVA through the heart and to the terminal HVB, and the discharge path BA is from the terminal HVB through the heart and to the terminal HVA. The entire discharge path BA includes the terminal CSP, the power FET 511, triac 510, diode 514, terminal HVB, the patient's heart, terminal HVA, power FET 919, and terminal CSN. Similarly, the discharge path AB is from the terminal CSP through power FET 527, triac 520, diode 522, terminal HVA, the patient's heart, terminal HVB, power FET 517 and terminal CSN.

Before explaining the switching of the power FETs and triacs, it should be noted that the power for the high voltage output circuit of FIG. 4B is obtained from the potential across terminals CSP and CSN by a power supply comprising the power FET and diodes within block U8. The components in block U8 are coupled to the VDD power line in order to provide a regulated 15 volts to the components and blocks U1–U4 which control the switching of power FET's 511, 517, 519, 527 and block U5 which controls internal discharge of C1, C2 (FIG. 4A) in response to a DUMP command.

The power FET's 511 and 527 are the high voltage side switching FET's whose on and off operation are controlled by opto-isolators 508 and 531 and switching blocks U4 and U3. The low power FET's 517 and 519 are switched on or off by the switching blocks U1 and U2 which, in addition, develop the switching signals for the opto-isolators 508 and 531, respectively. The triacs 510 and 520 are switched on by the surge in power at their "1" terminals and by the current drawn through the junction of the "1" terminals and the "3" terminals to charge the RC timing circuit components (capacitors 514, 515, 524, 525 and resistors 529, 533) coupled to each of the trigger input terminals "3" and VSS.

The ENBA signal is applied to terminal CSEN of driving circuit U1 and terminal VIN of driving circuit U2. The ENBA signal applied to terminal CSEN of VI provides a current drive signal out terminal CSOUT to the LED of opto-coupler 508, which in turn renders its optically coupled photo transistor conductive and connects the terminals VIN and CSEN of drive circuit U4 to its terminal OPTIN. When this occurs, a 14.5 volt signal developed from VDD is applied at the VOUT terminal to the gate of the power FET 511 to drive it into conduction and hold it in conduction for the duration of the ENBA signal. The ENBA signal is also applied to the VIN input terminal of drive circuit U2, which in turn provides the 14.5 volt signal at its VOUT terminal to the gate of FET 519. In this fashion, the BA discharge circuit path is rendered conductive.

In like fashion, the ENAB signal is coupled to the charge drive circuits U1, U2 and the opto coupler 531 to provide the AB discharge path by switching on FETS 517 and 527.

The DUMP signal is applied to the VIN input of the drive circuit U5 which couples its VDD terminal to its VOUT terminal and load resistor 504, which is preferably 1K ohm. The FET 532 in U8 has its source and gate normally biased at 17 volts by the zener diodes 533 and 534, respectively. The drain voltage may be from zero volts to 1,000 volts, depending on the state of charge of the capacitors C1, C2 (FIG. 4A). When the drain voltage exceeds 17 volts, the FET is rendered conductive with about a 2-3 volt drop across its drain and source terminals, causing the source terminal to present a nominal 15 volt value at terminal 4 of U8.

When the DUMP signal is present, the 15 volt signal is applied through the VDD terminal of U5 through a 1 volt drop to the VOUT terminal and resistor 504. Resistor 504 thus develops a 14 milliamp current to the source of the FET 532 in circuit U8, causing the voltage on C1, C2 to drain through the FET and the 1K 504 resistor over a relatively long period of time. In the absence of the DUMP signal and the drive circuit U5, the voltage on capacitors C1, C2 would self-discharge through the high impedance resistors 501, 502 over a period of minutes to hours.

The manner in which the duty cycle of the CHGDR signal is developed from the VCAP signal will now be explained in conjunction with FIGS. 5 through 7. The circuits depicted in FIGS. 5 through 7 represent various parts of low power hybrid 106 included in the digital IC's and discrete components contained therein.

FIG. 5 depicts a preferred embodiment of the CHGDR signal generator which responds to a CHGCLK signal in order to develop a relatively high current signal directly from the battery power source at terminal QBP. The high current CHGDR signal drives the power FET 124 of FIG. 4A into conduction very rapidly during the 11 microsecond (or 4 microsecond when the battery is depleted) "on" time and turns power FET 124 off hard to prevent its gate-to-drain stray capacitance from coupling voltage built up on the drain to the gate and turning FET 124 back on. Thus, the CHGDR signal is derived from the capacitors 550 and 551 through the N-channel and P-channel FET's 552, 553, 556 and 554, 555, 557, respectively. The N- and P-channel FET's are selectively turned on and off through signals developed from a non-overlap shifter (NOLS) circuit 558, a level shifter 559, and the drive inverters 560 and 561–567 coupling the output of the NOLS or LSI circuits to the gates of the FET's.

The NOLS circuit 558 receives the CHGCLK signal (developed by the VCO of FIGS. 7 and 8 at its input terminal and provides non-overlapping signals at its output terminals, which selectively render certain of the P-channel and N-channel FET's conductive to develop the high current charge drive CHGDR signal which varies with the duration and frequency of the CHGCLK signal to be described hereafter.

The charge driver circuit of FIG. 5 drives the gate of FET 124 of FIG. 4A via its CHGDR output. When CHGCLK is low, CHGDR is driven to QVSS via FET 555. When CHGCLK is high, CHDR is driven to a voltage equal to:

$$QBP*\left(1 + \frac{C551}{C550 + C551} \cdot \frac{C550}{C550 + C_L}\right), \quad \text{(EQUATION A)}$$

Where
$C_L$ = gate capacitance of FET 124, and
$C551 >> C550 >> C_L$

The creation of this large positive voltage on CHGDR is explained as follows. When CHGCLK is low, Capacitor 551 (which was precharged to QBP, QCPIP to QCPIM, when CHGCLK was high) is connected with Capacitor 550 (their negative terminals tied together and their positive terminals tied to QVSS). Thus C550 is charged to a voltage equal to:

$$QBP * \frac{C551}{C550 + C551} \quad \text{(EQUATION B)}$$

When CHGCLK is high, Capacitor 551 is again precharged to QBP while Capacitor 550's negative terminal is driven to QBP and its positive terminal is connected to CHGDR; it is during this time that CHGDR (and FET 124 of FIG. 4A) is driven to the large positive voltage indicated in equation A. Thus, the "off" time occurs while CHGCLK is low (CHGDR is at QVSS); and the "on" time occurs when CHGCLK is high (CHGDR) is bootstrapped above QBP).

Turning now to FIG. 6, simplified block diagram of the VCO and its associated system components for developing the CHGCLK (and other signals) is depicted. The block diagram of FIG. 6 develops the variable frequency CHGCLK signal in response to the CHGEN signal and the VCAPIN signal applied to the VCNVRT block 306. The CHGEN signal is applied to the VCNVRT block 306, the VCO block 302, and the TDET block 300. Certain other signals are applied to blocks 300 to 306, which include the voltage reference (VREF) and the battery potential divided by two (DIVBP) signals, both applied to block 300, the IOSC25 and OSCTRIM signals applied to the oscillator bias (OCSBIAS) block 304, and the IVCC14 ground signal applied to block 306.

Very generally, the VCNVRT block 306 converts the VCAPIN signal to a current signal IBLVCOV which is applied to the VCO block 300. The OCSBIAS block 304 provides certain DC bias voltages to the VCO block 302 and the VCNVRT block 306. The TDET block 300 provides a signal NTD to the VCO 302 and a signal NTDEN to other circuit components not relevant here. The NTD signal value (high or low) selects the VCO on-time to be either 11 microseconds in a normal range of battery voltage or 4 microseconds when the battery voltage depletes below the VREF threshold as compared to the DIVBP signal.

Thus, the VCO block 302 responds to the CHGEN input signal, the state of the NTD signal, the DC bias VNCIB, the DC bias VBVCO, and the current signal IBLVCOV developed by the VCNVRT block 306 to provide the CHGCLK signal to the charge drive circuit of FIG. 5. The TDET block 300, the VCO block 302, the OSCBIAS block 304, and the VCNVRT block 306 are depicted in FIGS. 7A–7D and 8A–8C described hereinafter.

Figure 7B:
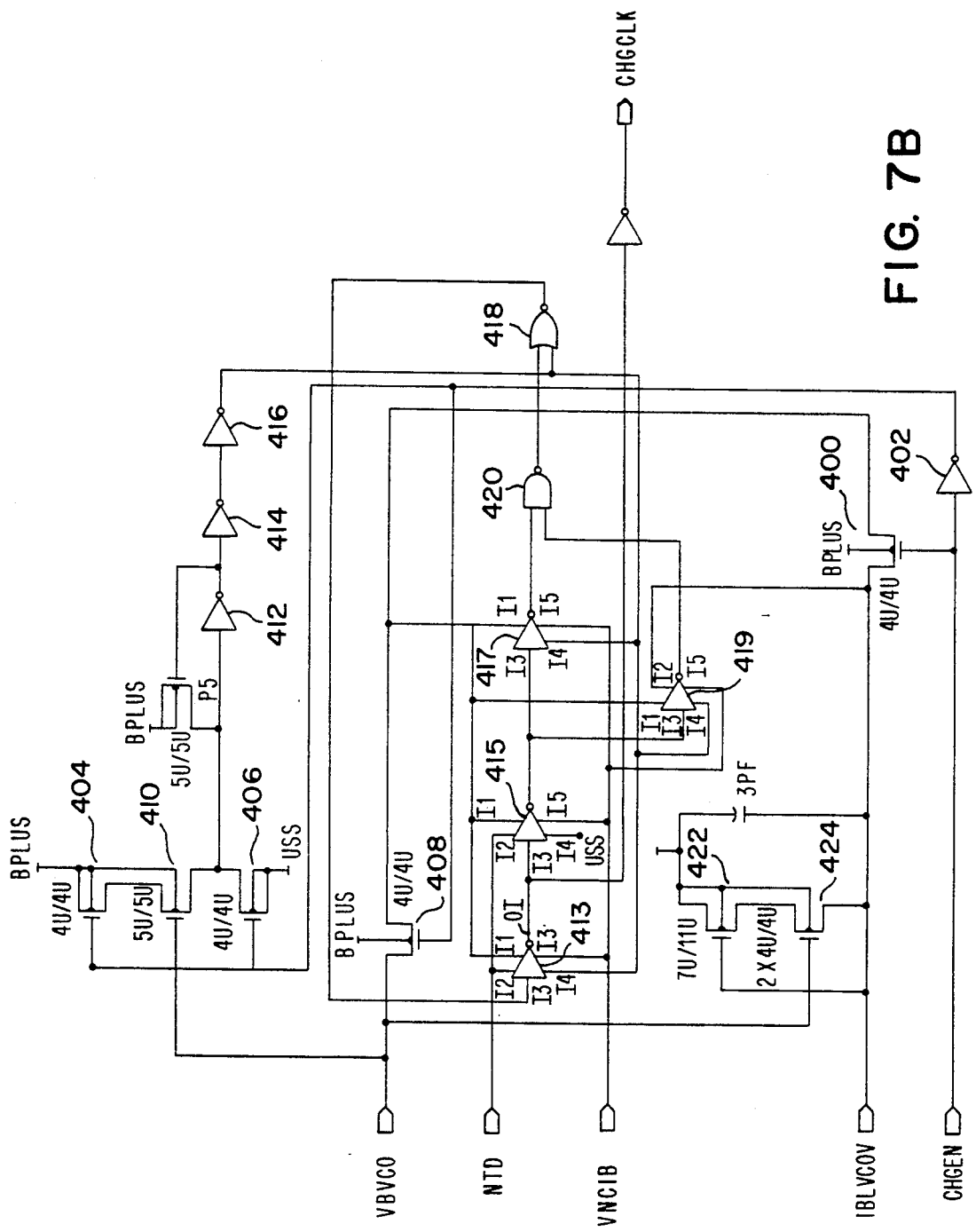

Turning now to FIG. 7A, the TDET block 300 is shown in greater detail. Very generally, whenever the CHGEN signal is present, the differential amplifier 310 is enabled to compare a sampled value of one-half the actual battery potential (DIVBP) to the VREF signal. The battery potential is sampled by the CHGCLK signal toggling a flip-flop 312, which first closes a transmission gate 314 and then opens transmission gate 314 and closes transmission gate 316. When transmission gate 314 is closed, DIVBP is sampled by capacitor 318, and when transmission gate 316 is closed, that sampled value is applied to the positive input of differential amplifier 310. If that sampled value is greater than the VREF value (nominally 1.2 volts), then the NTD signal is "high." Conversely, if the VREF signal value is greater than the sampled DIVBP signal value, then the NTD signal is switched "low." The NTD signal is applied to one input of the VCO block 302 depicted in FIG. 7B.

Turning to FIG. 7D, the VCNVRT circuit block is depicted in detail. The circuit in FIG. 7D converts the VCAPIN signal voltage, in conjunction with IB235NS, into the IBLVCOV bias signal which controls the "off" time via the DELVAR delay stage 419 in FIG. 7B. When CHGEN is low, Op AMP 330 is disabled and its positive input is grounded (i.e., pulled to AVSS) via N-channel MOSFET 332. Thus, N-channel MOSFET 324 has only the current IB235NS going through it. This current in MOSFET 324 sets up a voltage which causes N-channel MOSFET 328 to carry a current which is equal to IB235NS. This current passes through N-channel MOSFET 326 to bias DELVAR delay stage 419 in FIG. 7B, to have a 235 ns delay from its input going low to its output going high.

When CHGEN is high, op amp 330 is enabled. When op amp 330 is enabled the current through MOSFET 324 can be increased in direct proportion to VCAPIN.

When VCAPIN equals 0, IBLVCOV continues to carry only a current equal to IB235NS. However, when VCAPIN is greater than zero volts, the current through N-channel MOSFET 322 equals VCAPIN/R572 (R572 is a 4.28 Mohm resistor depicted in FIG. 6). The current in MOSFET 322 is summed with the current of IB235NS to create a voltage which causes MOSFET 328 to carry a current which is equal to IB235NS+-VCAPIN/R572. Thus, as VCAPIN increases, the bias current to DELVAR delay stage 419 in FIG. 7B increases, which decreases the delay from its input going low to its output going high. Therefore, the "off" time as generated in DELVAR follows the equation on page 9.

Figure 7C:
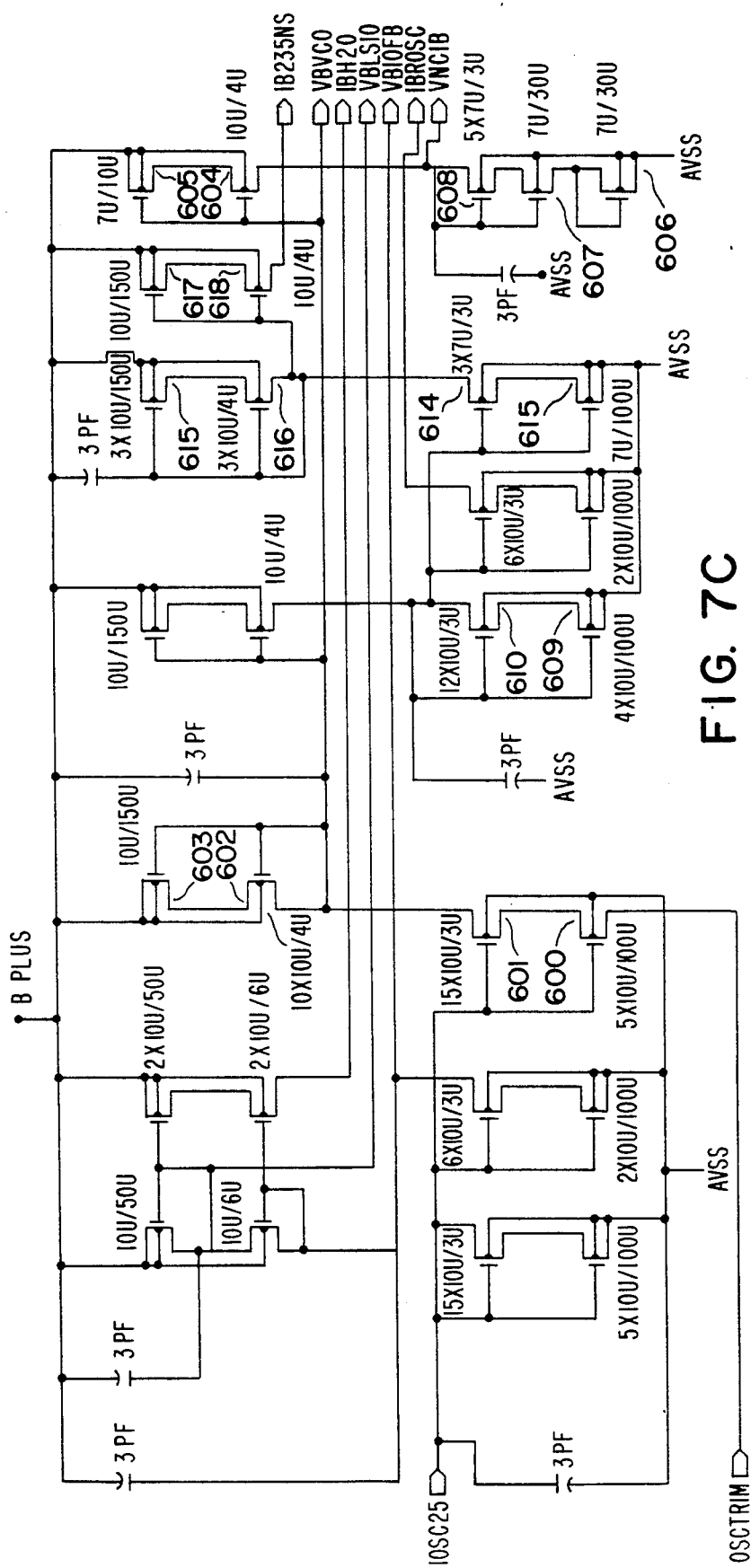

The circuitry in the oscillator bias block 304 (FIG. 6) is illustrated in FIG. 7C. The voltage created at VBVCO is formed by the current defined by FET's 600 and 601 passing through FET's 602 and 603. This current is established by adjusting a trim resistor (R570 in FIG. 6) connected between AVSS (analog ground) and the source of FET 600. The nominal current value is 10nA, which is sufficient to establish appropriate currents in the delay stages of FIG. 7B. FET's 604 and 605 establish a voltage at VNC1B by supplying approximately 10nA to FET'S 606, 607 and 608; this voltage is approximately the sum of 2 N-channel thresholds.

The controlled current on line IB235NS is also generated in FIG. 7C. This current is generated by passing approximately 10nA through diode wired FET'S 609 and 610 to create a voltage to bias FET'S 613 and 614. FET'S 613 and 614 sink approximately 1.67 nA from diode wired FET'S 615 and 616. Thus a voltage is created at the drain of P7 and the gates of P7 and P7A which is used to bias FET'S 617 and 318, which supply approximately 0.55nA to the IB235NS line.

Other signals depicted in the circuit of FIG. 7C are used for the control of other operations of the system as a whole not relevant to the explanation of the voltage control oscillator of the present invention.

Turning now to the VCO circuit of FIG. 7B, it generates the variable duty cycle CHGCLK signal when enabled by the CHGEN signal and in response to the state of the NTD signal and the IBLVCOV signal which is related to the VCAPIN signal. Biasing signals, VBVCO and VNCIB which are relatively constant, operate in conjunction with the depicted components to provide a CHGCLK signal with an "on" time of preferably 11 microseconds when the NTD state is high and 4 microseconds when the NTD state is low and an "off" time which is inversely proportional to the magnitude of the VCAPIN signal. The heart of the oscillator is constructed from the DELVAR5, DELVAR3 and DELVAR delay stage inverters 413, 415, 417 and 419 in conjunction with NAND gate 420 and NOR gate 418 which are connected in FIG. 7B to function as a low current drain, high speed oscillator for generating the CHGCLK signal.

Figure 8A:
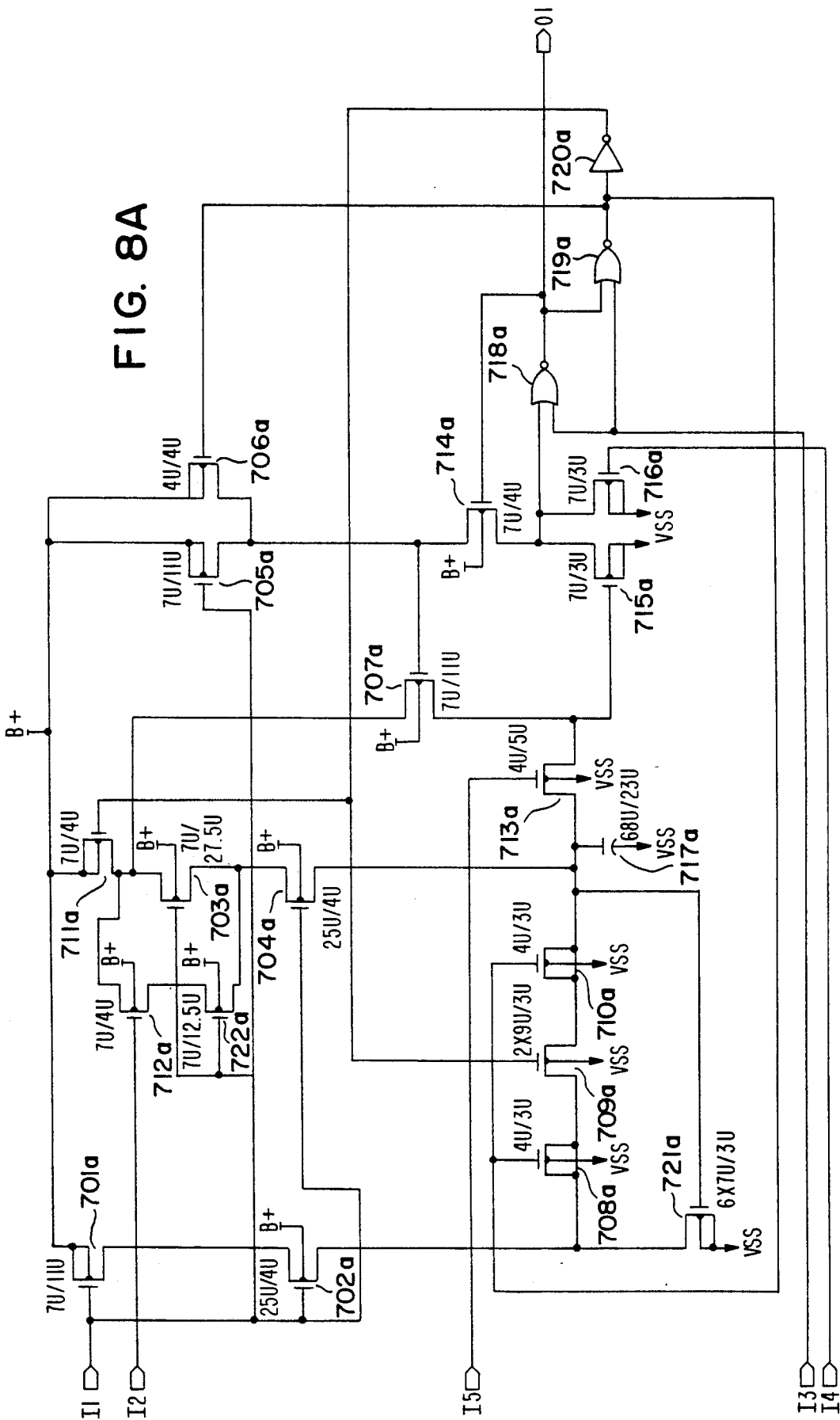

DELVAR5 invertor delay circuits 413 and 415 are shown more specifically in FIG. 8A. DELVAR3 invertor circuit 417 is shown more specifically in FIG. 8B. DELVAR Invertor delay circuit 419 is shown in greater detail in FIG. 8C. In all of the circuits of FIGS. 8A to 8C, the input terminals I1-I5 are connected as shown in FIG. 7B.

FIG. 7B illustrates the oscillator loop defined by the series connected delay circuits 413, 415 and 417, the NAND gate 420 and the NOR gate 418. Each delay circuit defines a controlled delay between the negative going transition of the logic level of the signals applied to their 13 inputs and the corresponding positive going transition of the logic level signal signals at their outputs.

The delay circuits 413 and 415 are otherwise referred to as DELVAR5 circuits. The DELVAR5 circuits each define a fixed 5.5 microsecond delay signal when DIVBP (FIG. 7A) is greater than VREF and define a 2 microsecond delay signal when DIVBP is less than VREF. When connected in series as shown, the on-time of the CHGCLK signal is developed from the summed 5.5 microsecond or 2.0 microsecond periods of delay circuits 413 and 415.

The off-time of CHGCLK is developed by the greater of the fixed delay provided by DELVAR3 delay circuit 417 or DELVAR delay circuit 419 connected in parallel and having their terminals coupled to input terminals of NAND gate 420. DELVAR3 delay circuit 417 defines a fixed delay of 3 microseconds. DELVAR delay circuit 419 defines a variable delay varying between 1 microsecond when VCAP equals 1,000 volts to 235 microseconds when VCAP equals zero.

Figure 9:
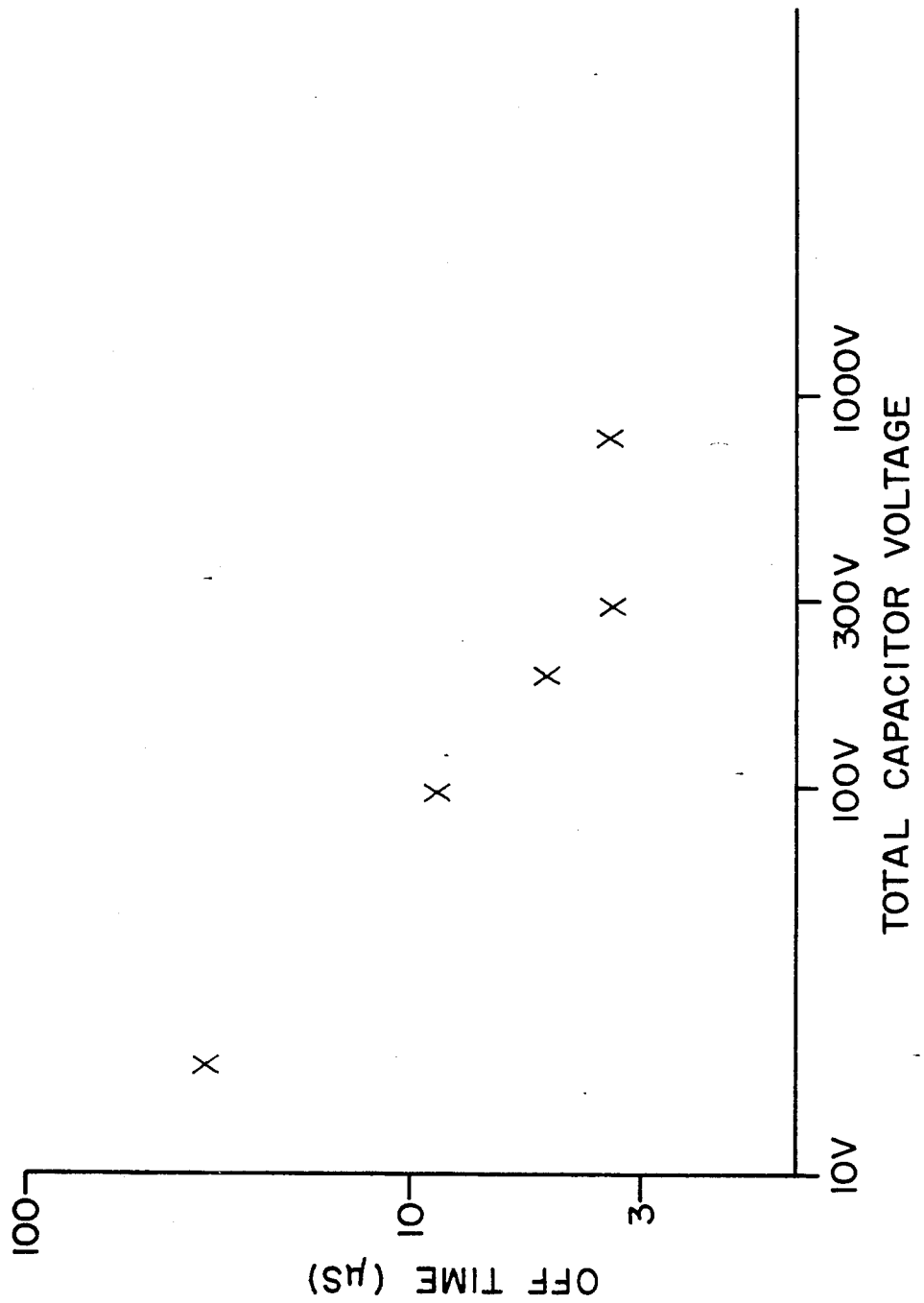
FIG. 9 depicts the VCO transfer function of the off-time to the high voltage output capacitor voltage during charging thereof.

The pulse width of the signal delivered by DELVAR delay 419 is a function of the value of the IBLVCOV signal applied through its input terminal I2 when the CHGEN signal is applied to the circuit of FIG. 7B and to the other blocks of FIG. 6, specifically the TDET block 300 illustrated in FIG. 7A and the VCNVRT block 306 illustrated in FIG. 7D. The interval between successive CHGCLK 11 microsecond or 4 microsecond pulses ("on" times) thus varies between 3 microseconds and 235 microseconds as provided by the greater of the 3 µs fixed delay of delay 417 or the variable delay of delay 419. When VCAP is zero and the CHGEN signal is first applied, the cycle length of the CHGCLK signal is thus 235 microseconds plus 11 (or 4) microseconds. As VCAP increases, IBLVCOV increases and delay 419 provides a progressively shorter delay until the cycle length is reduced to the sum of 11 microseconds (or microseconds) plus 3 microseconds provided by delay 417. As shown in FIG. 9, the 3 microsecond interval provided by delay 417 will control when the VCAPIN signal reflects a voltage of 300 volts or more on capacitors C1, C2 of FIG. 4B. Although not specifically shown in the logarithmic scale of FIG. 9, the off-time supplied by delay 419 between zero and 10 volts varies from 235 to about 60 microseconds.

Returning now to FIG. 7B, in the absence of a CHGEN signal CHGEN low), FET 400 is conductive and FET 408 is non-conductive. Conversely, when CHGEN is present, FET 400 is rendered non-conductive and FET 408 is rendered conductive to allow the application of a fixed VBVCO bias signal to terminals I1 of delay circuits 413, 415, 417 and 419. At the same time, the inverted CHGEN signal applied by invertor 402 to the gates of FETs 404 and 406 allows the application of BPLUS to the cascaded inverters 412, 414 and 416 to enable NOR gate 418 in order to complete the oscillator loop and applies a signal to the I4 terminal of delay 413, delay 419 delay 417. If the output of invertor 416 is high, the oscillator loop is held in a fixed state.

The IBLVCOV signal is applied to a current-to-voltage converter comprising FET's 422, 424 and capacitor 426 coupled to BPLUS which provides the bias signal to terminal I2 of delay 419. In addition, the VBVCO signal is applied to the gates of FET's 410 and 424 in order to limit the current in the invertor formed by 404 and 406 and to bias the cascode device 424, of the current to voltage converter comprising FET's 422 and 424. When FET 400 is on and FET is off, the IBLCOV signal is applied to the I1 input of all delays to limit static current drain while CHGEN is low.

Figure 8B:
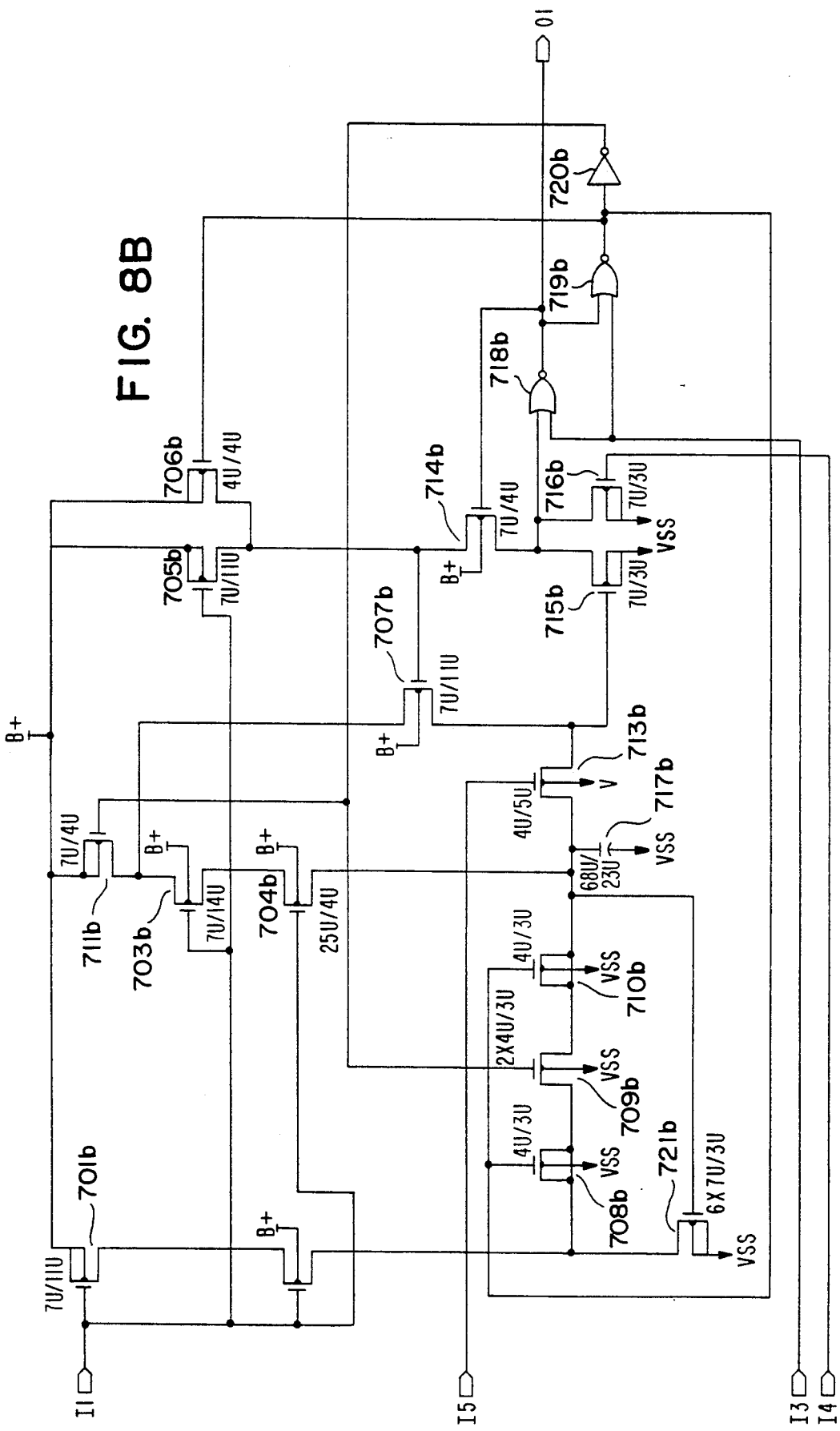

Turning now to FIGS. 8A to 8C, preferred embodiments of the delay circuits of FIG. 7B are depicted. Input signals to FIGS. 8A to 8C are identified in relation to the terminals depicted in FIG. 7B. The functions associated with inputs I1-I5 for the circuits illustrated in FIGS. 8A, 8B and 8C are as follows:

FIG. 8A

I1: establishes bias for current sources formed by FET's 701a, 702a, 722a, 703a and 704a.

I2: NTD input. When "high", the current source FET 722a is enabled—thus enabling faster charge rate into capacitor 717a. This permits shift from 5.5 μs delay to 2 μs delay (i.e., 11 μs "on" time shifts to 4 μs "on" time).

I3: Logic input

I4: Preset input. When high, FET 716a is a "on", which forces its drain to VSS. In conjunction with a low signal on I3, this forces the delay stage into a known state—O1 is high.

I5: VNCIB. Limits the maximum voltage to which capacitor 717a may charge; VNC1B sets a gate voltage on FET 713a such that it cannot pass a voltage to capacitor 717a which is more than approximately 0.2s higher than the voltage established across FET's 721a, 708a, 709a and 710a when FET 709a is "on".

FIG. 8B

I1: establishes bias for current sources formed by FET's 701b, 702b, 703b and 704b.

I2: not used for 8B.

I3: Logic input

I4: Preset input. Same as for 8A

I5: VNCIB: Same as for 8A

FIG. 8C

I1: establishes bias for current source formed by FET's 701c and 702c. Established bias for cascode device, FET 704c, to current course formed by FET 703c.

I2: establishes bias for current source formed by 703c. FET 703c is the current source controlled by IBLVCOV.

I3: Logic input.

I4: Preset input. Same as for 8A

I5: VNC1B: Same as for 8A

Each of the circuits of FIGS. 8A to 8C operate on the same principle and consequently, only FIG. 8A is described completely and differences in the operation of FIGS. 8B and 8C are noted. Turning to FIG. 8A, if I3 is held high (>3 us for normal operation), O1 is low, NOR gate 719a's output is low, and invertor 720a's output is high. Thus, during the time I3 is held high, the following a. Capacitor 717a is charged to approximately 1 N-channel threshold via the current source formed by FET's 722a and 702a. In effect, capacitor 717a is charged to the voltage of diode wired FET 721a, driven by the current of FET's 701a and 702a.

b. FET 711a is off. Thus, the current sources formed by FET's 703a and 722a are disabled. FET 712a is controlled by I2 (which is connected to NTD), and enables the current source formed by FET 722a when I2 is low. Only DELVAR5 includes FET's 712a and 722a, which make it possible to switch the delay defined by the circuit from a 5.5 μs delay to a 2 μs delay if the NTD signal on input I2 is low.

c. FET 714a is on because NOR gate 718a has a logic 0 output. FET 706a is on because NOR Gate 719a has a logic 0 output. Thus, the drains of FET's 715a and 716a are high and the gate of FET 707a is high.

d. FET 715a's gate has the same voltage on it that is on capacitor 717a. However, the drain of FET 715a is held high because FET 705a supplies the same current as FET 701a supplies and FET 715a has only 1/6 the transistor size of FET 721a, and because FET's 706a and 714a are on. Even after FET 706a is turned off, the drain of FET 715a will remain high until the voltage on capacitor 717a increases by $n*V_T \ln(6)$, which makes FET 715a capable of sinking the current through FET 705a. Thereafter the drain of FET 715a can start to fall toward ground. However, this cannot occur until FET 711a is turned on to allow FET 703a, FET 722a (if NTD is low), and FET 704a to charge capacitor 717a beyond its initial voltage.

e. I4 is normally low. It is held high only to force the drain of FET 715a low during the time the oscillator is held in a fixed state when the output of invertor 416 (of FIG. 7B) is high.

When I3 goes low, the following events occur:

a. The output of NOR gate 719a goes high, because O1 is already low. Thus the output of invertor 720a also goes low.

b. FET 706a turns off. FET 714a remains on. The drain of FET 715a remains high for a period of time as described in (d) above.

c. FET 709a turns off, and FET 711a turns on. Thus capacitor 717a is allowed to charge to a higher voltage.

d. The gate of FET 715a follows the voltage on capacitor 717a until the change in voltage is sufficient to cause FET 715a to pull its drain toward ground. Again, this required voltage change is $n * VT \ln(6)$.

e. As FET 715a's drain is pulled low, FET 707a starts conducting. Thus, the voltage rise at the gate of FET 715a begins to accelerate. This positive feedback causes the gate of FET 715a to rise rapidly while the drain of FET 715a falls rapidly.

f. The voltage on capacitor 717a ceases to follow the voltage of FET 715a's gate at approximately 1 N-channel threshold plus approximately 200 mV, because the voltage on VNC1B equals approximately 2 N-channel thresholds plus 200 mV. As FET 713a ceases to transfer charge to capacitor 717a, the rate of voltage increase on the gate of FET 715a increases; thus accelerating the rate at which the drain of FET 715a falls, which, in turn, further increases the rate at which the gate of FET 715a increases. Thus, FET 713a assures that the positive feedback described in e (above) occurs more rapidly than if capacitor 717a had to be charged at the same time. Also, limiting the maximum voltage on capacitor 717a makes resetting its voltage to is original value easier.

g. When the drain of FET 715a goes low O1 goes high and FET 714a is turned off. The output of NOR gate 719a goes high, and the output of invertor 720a goes low. The delay between the negative transition on the I3 input and the positive going transition of O1 is 5.5 microseconds if I2 (NTD) is high and 2 microseconds if I2 is low.

h. FET 706a is turned on, which forces the source of FET 714a high and turns FET 707a off.

i. FET 711a is turned off, and FET 709a is turned on. Thus capacitor 717a and FET 714a's gate are allowed to charge to their original level prior to I3's going low.

When I3 goes high again, the following events occur:

a. 01 goes low, and FET 714a turns on.

b. The drain of FET 715a goes high.

c. The output of NOR gate 719a stays low, and the output of invertor 720a stays high.

d. The delay stage is now reset and ready for the next time I3 goes low.

The delay circuit of 417 as illustrated in FIG. 8B operates in substantially the same fashion as the circuit of FIG. 8A. The principal difference between the two resides in the fact that the parallel current source path which is controlled by the signal NTD, comprising FET's 712a and 718a in FIG. 8A is deleted. The die size of FET 703b in the delay circuit of FIG. 8B is also modified so that the delay circuit provides a fixed 3 microsecond delay in switching its output at output terminal 01 in response to a negative going output signal 01 of the delay circuit 415 of FIG. 7B.

Similarly, the delay circuit of FIG. 8C operates in substantially the same fashion, the only difference being that the signal IBLVCOV is applied to FET 703c of the current source for capacitor 717c instead of the constant bias voltage VBVCO. Thus, the FET 703c in the delay circuit of FIG. 8C is rendered more or less conductive in dependence on magnitude of the IBLVOV signal.

As shown graphically in FIG. 9, the off-time of the CHGCLK signal between successive 11 microsecond or 4 microsecond on-time pulses varies as a function of the VCAP value. If the VCAP value is charged up to between 300 volts and 1000 volts, the off-time is constant at 3 microseconds. Between 10 volts and 300 volts charge, the off-time varies from about 60 microseconds at 10 volts to 8.5 microseconds at 100 volts, and to 3 microseconds at 300 volts. Thus, the VCO circuit is called upon to switch between high and low states very rapidly and to do so with a minimal current drain in order to preserve battery potential in an implanted device. Consequently, the time delay circuits are designed as shown in FIGS. 8A to 8C to employ extremely small voltage swings on their timing capacitors 717a, 717b, 717c, with extremely small amounts of current dissipated in the charging and discharging of the timing capacitors.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications and alterations should therefore be seen within the scope of the present invention.

What is claimed is:

1. A medical device for the electrical termination of an arrhythmic condition of the heart, comprising:
   a battery;
   a capacitor for storing voltage;
   means for delivering voltage stored on said capacitor to cardiac tissues;
   transformer means for providing charging current to said capacitor;
   voltage sensing means coupled to said capacitor for sensing the voltage level stored on said capacitor and for generating a capacitor voltage signal indicative thereof;
   voltage controlled oscillator means for coupling and uncoupling said transformer means from said battery, said oscillator means further comprising timing means defining on times during which said transformer means is coupled to said battery and off times during which said battery is uncoupled from said transformer means as a function of said capacitor voltage signal such that as said capacitor voltage signal indicates that the voltage level stored in said capacitor increases, the frequency of occurrence of said on times increases correspondingly and the durations of said off times simultaneously decrease.

2. The device of claim 1 wherein:
   said voltage controlled oscillator means defines said on times to have durations which do not vary as a function of the voltage stored in said capacitor and defines said off times to have a duration which varies inversely to the voltage stored in said capacitor.

3. The device of claim 1 or claim 2 wherein said battery provides a voltage which decreases as said battery is depleted and wherein said oscillator means further comprises means responsive to the voltage provided by said battery falling below a predetermined level for reducing the on times defined by said oscillator means to facilitate charging of said capacitor when said battery has been significantly depleted.

4. A medical device for the electrical termination of an arrhythmic condition of the heart, comprising:
   a battery;
   a capacitor for storing voltage;
   means for delivering voltage stored on said capacitor to cardiac tissue;
   transformer means for providing charging current to said capacitor;
   first voltage sensing means for sensing the voltage stored on said capacitor and for generating a capacitor voltage signal indicative thereof;
   second voltage sensing means for sensing the voltage level of said battery and for generating a battery voltage signal indicative thereof;
   voltage controlled oscillator means for coupling and uncoupling said transformer means from said battery, said oscillator means comprising timing means defining on times during which said transformer means is coupled to said battery and off times during which said battery is uncoupled from said transformer means as function of both said battery voltage signal and said capacitor voltage signal.

5. A device as in claim 4 wherein said voltage controlled oscillator means varies said on times and said off times such that as said capacitor voltage signal indicates that the voltage level stored in said capacitor increases, the frequency of occurrence of said on times increases correspondingly and the durations of said off times simultaneously decrease and such that as said battery voltage signal indicates that the voltage level of said battery decreases, said on times decrease.

6. A device as in claim 4 wherein said oscillator means comprises:
   a plurality of delay circuits connected in series to form an oscillator loop, at least a first one of said delay circuits defining said on times, at least a second of said delay circuits defining said off times.

7. A device according to claim 6 wherein said first one of said delay circuits is responsive to said second voltage sensing means and defines said on times as a function of said battery voltage signal.

8. A device according to claim 6 wherein said second one of said delay circuits is responsive to said first voltage sensing means and defines said off times as a function of said capacitor voltage signal.

9. A device according to claim 8 wherein said oscillator means further comprises at least a third delay circuit defining a fixed duration off times, connected in parallel to said second one of said delay circuits and logic means for selecting tho longer of the off times defined by said second one of said delay circuits and said third delay circuit.

10. A device according to claim 1 or claim 4, wherein said oscillator means comprises:
a plurality of FET invertor delay circuits, each having a logic input and a logic output, connected in series to form an oscillator loop, at least a first one of said delay circuits defining said on times, at least a second of said delay circuits defining said off times, said first and second ones of said delay circuits each comprising a timing capacitor, a first FET means for charging said timing capacitor to a first charge level, a second FET means for charging said capacitor to a second level in response to a logic level transition at said logic input and a third FET means responsive to the charging of said timing capacitor to said second level for causing a corresponding logic level transition at said logic output, at least one of said first and second ones of said delay circuits provided with means for varying the current drawn through said second FET means to vary the time required for the charge on said timing capacitor to reach said second level.

11. An device as in claim 10 wherein said first and second ones of said delay circuits are both provided with means for varying the current through said second FET means.

12. An oscillator as in claim 10 wherein said means for varying said current through said second FET means comprises means for varying the voltage provided to a gate of an FET within said second FET means.

13. An oscillator as in claim 10 wherein said means for varying current through said second FET means comprises means for selecting between multiple FET's within said second FET means for delivery of said current.

14. A device according to claim 10 wherein said oscillator means further comprises at least a third delay circuit defining fixed duration off times, connected in parallel to said second one of said delay circuits and logic means for selecting the longer of the off times defined by said second one of said delay circuits and said third delay circuit.

* * * * *